United States Patent
Grüning et al.

(10) Patent No.: US 7,595,181 B2
(45) Date of Patent: Sep. 29, 2009

(54) THERMOSTABLE ESTERASES FROM THERMOPHILIC BACTERIA

(75) Inventors: Burghard Grüning, Essen (DE); Geoffrey Hills, Essen (DE); Thomas Veit, Hagen (DE); Christian Weitemeyer, Essen (DE); Olivier Favre-Bulle, Nimes (FR); Fabrice Lefevre, Nimes (FR); Hong-Khanh Nguyen, Nimes (FR); Gilles Ravot, Nimes (FR)

(73) Assignee: Proteus S.A. (FR)

( * ) Notice: Subject to any disclaimer, the term of this patent is extended or adjusted under 35 U.S.C. 154(b) by 424 days.

(21) Appl. No.: 10/954,826

(22) Filed: Sep. 30, 2004

(65) Prior Publication Data
US 2005/0112644 A1 May 26, 2005

(30) Foreign Application Priority Data
Sep. 30, 2003  (EP) .................................. 03021972

(51) Int. Cl.
C12N 9/18 (2006.01)
C07K 14/195 (2006.01)
C12P 21/02 (2006.01)
C12P 7/64 (2006.01)

(52) U.S. Cl. ............... 435/197; 530/350; 435/69.1; 435/134

(58) Field of Classification Search ............ 435/197, 435/69.1, 134; 530/350
See application file for complete search history.

(56) References Cited

U.S. PATENT DOCUMENTS

| | | | |
|---|---|---|---|
| 5,173,417 A | 12/1992 | Takeda et al. | |
| 5,306,636 A | 4/1994 | Iizumi et al. | |
| 5,480,787 A | 1/1996 | Negishi et al. | |
| 5,714,373 A | 2/1998 | Stetter | |
| 5,766,912 A | 6/1998 | Boel et al. | |
| 5,846,801 A | 12/1998 | Kotsuka et al. | |
| 2002/0146799 A1 | 10/2002 | Robertson et al. | |

FOREIGN PATENT DOCUMENTS

| | | | |
|---|---|---|---|
| EP | 0 117 553 | | 9/1984 |
| EP | 0 709 465 | | 5/1996 |
| EP | 0 714 984 | | 6/1996 |
| WO | WO 97/30160 | * | 8/1997 |

OTHER PUBLICATIONS

EC 3. Hydrolase Nomenclature, Nomenclature Committee of the International Union of Biochemistry and Molecular Biology (NC-IUBMBO, print out form http://www.chem.qmul.ac.uk/iubmb/enzyme/EC3/, Apr. 16, 2007.*

Result 1, search in protein sequence database of published U.S. applications (rapbn.), Imanaka et al. (US 2006/0248617 A1), SEQ ID No. 518, esterase from Thermococcus kodakaraensis, priority date of Aug. 30, 2002, alignment of instant SEQ ID No. 3 with SEQ ID No. 518 from Imanaka et al. (86.6% sequence identity), searched on Mar. 9, 2007.*

Badalassi, Wahler, et al., "A Versatile Periodate-Coupled Fluorogenic Assay for Hydrolytic Enzymes" Angew. Chem. Int. Ed. Engl. 2000, 39, 4067.

(Continued)

*Primary Examiner*—Delia M. Ramirez
*Assistant Examiner*—Rosanne Kosson
(74) *Attorney, Agent, or Firm*—Hunton & Williams LLP

(57) ABSTRACT

The present invention relates to a newly identified hydrolase from thermophilic microorganisms having thermostable properties, and more specifically, to a novel thermostable hydrolase showing high activity at high temperatures.

10 Claims, 3 Drawing Sheets

Transesterification of methyl laurate with decanol and free Est P 1021

OTHER PUBLICATIONS

Cagnon, Valverde, et al., "A New Family of sugar-inducible Expression Vectors for *Escherichia coli*", Protein Engineering, 1991, 4(7), 843-7.

Cornec L., et al., "Thermostable esterases Screened on Hyperthermophilic Archaeal and Bacterial Strains Isolated from Deep-Sea Hydrothermal Vents: Characterization of Esterase Activity of a Hyperthermophilic Archaeum, Pyrococcus abyssi", Journal of Marine Biotechnology, 1998, 6(2),104-110.

Fernandez-Lafuente, et al., "Hyperstabilization of a thermophilic Esterase by Multipoint Covalent Attachment" Enzyme and Microbial Technology, 1995, 17 (4), 366-372.

Hotta, et al., "Extremely Stable and Versatile Carboxylesterase from a Hyperthermophilic Archaeon", Appl. Environ. Microbiol., 2002, 68 (8), 3925-3931.

Ikeda, Clark, "Molecular cloning of extremely thermostable esterase gene from hyperthermophilic archaeon pyrococcus furiosus in *E coli*", Biotechnology and Bioengineering, 1998, 57, 6249.

Lagarde, D. et al., "High-Throughput Screening of Thermostable Esterases for Industrial Bioconversions", Org. Proc. Res. Dev., 2002, 6 (4), 441-445.

Sambrook, J. et al., Molecular Cloning, A Laboratory Manual, 2nd Ed., Cold Spring Harbour Laboratory, 1989.

Santaniello, et al., "Lipase-catalyzed transesterification in organic solvents: Applications to the preparation of enantiomerically pure compounds", Enzyme Microb. Technology, 1993, vol. 15, May 93 pp. 367-382.

Wahler, Badalassi, et al., "Enzyme Fingerprints by Fluorogenic and Chromogenic Substrate Arrays" Angew. Chem. Int. Ed., 40, p. 4457, 2001.

Watanabe, Ota, et al., "Isolation and identification of alcaline lipase producing microorganisms, cultural conditions and some properties of crude enzyme", Agric. Biol. Chem., 1977, 41, 1353-1358.

Database Embl XP002270381 2003, Robertson et al.,Thermococcus CL-2 30LC esterase, GenEmbl No. ABU56926.

Niehaus, et al., "Extremophiles as a Source of Novel Enzymes for Industrial Application", Appl. Microbiol. Biotechnol., vol. 51, pp. 711-729, (1999).

Santaniello, et al., "The Biocatalytic Approach to the Preparation of Enantiomerically Pure Chiral Building Blocks", Chemical Reviews, American Chemical Society, vol. 92, No. 5, pp. 1071-1140, (1992).

* cited by examiner

Map of the vector pARA 1021

Transesterification of methyl laurate with decanol and free Est P 1021

Determination of the activity of immobilised recombinant Est P 1021

SEQUENCE LISTING

<160> NUMBER OF SEQ ID NOS: 6

<210> SEQ ID NO 1
<211> LENGTH: 768
<212> TYPE: DNA
<213> ORGANISM: Pyrococcus

<400> SEQUENCE: 1

```
atgatattca aggccaagtt cggagagcca aagagaggat gggtagttat agtgcacggc      60
ctgggagagc acagcgggag gtacgcgaag ctcgttgaaa tgctagttga gagggqcttt     120
gcggtatata catttgactg gcctgggcat ggaaagagct ccggaaagag aggacacaca     180
agtgttgagg aggcaatgga gataattgac gaaattattg aggagatcgg ggaaaagccg     240
ttcctatttg ggcacagctt aggtgggcta accgtcataa ggtacgcaga aacaaggccc     300
gagaaggtga agggagttat agcctcttca ccagcgttgg caaagagccc aaacacccca     360
ggatttctag ttgcgttggc gaagttctta ggggttgtgg ccccaggaat tacgttttct     420
aatggaatta acccgaactt actctcaagg aacaaggatg cggtgaggag gtacgtagaa     480
gatcccttgg ttcacgacaa aatcacggca aagctcggaa ggagcatatt catgaacatg     540
gagcttgccc acagggaagc cgagaaaatc aaagtgccaa tcctgctctt agtaggaacc     600
caagacgtca taacgccccc cgaaggagcc agaaaattgt ttgaaaaact caaagttgaa     660
gacaaagaga ttagagaatt cgagggagct taccatgaga tatttgagga tccggagtgg     720
ggagaagaat tccatagggt gatagtggag tggctggaga agcacagt                  768
```

<210> SEQ ID NO 2
<211> LENGTH: 783
<212> TYPE: DNA
<213> ORGANISM: Thermococcus

<400> SEQUENCE: 2

```
atggaggttt acaaagttag gtttggaact cccgagaggg gctgggtcgt tctggtgcac      60
ggtcttggag agcacagcgg acgctacgga aggctgatta gctgttaaa cgagaacggt     120
tttggcgttt acgccttcga ctggcccgga cacggaaaaa gccctggcaa gaggggccac    180
accagcgttg aggggctat ggaaataatt gattccataa ttgaagaatt aggtgaaaat     240
cccttcctct tcggccacag ccttggaggt ttaaccgtca tccgctatgc agaggcgagg    300
ccagataaga taaggggcgt catcgcctca tcaccggccc tcgcgaagag ccccgaaacg    360
ccggacttta tggtcgcttt ggcaaagttc ctcggaagga tcgcaccggg tttaactctc    420
tccaacggca taaagccgga actcctttcc agaaacaggg acgccgtgag gaggtacgtg    480
gaggatccac tcgttcacga cagaatttcg gcaaagcttg gaaggagcat attcgtcaac    540
atggatctgg cccacaggga gcggagaat ataaggggtc caattctact actcgttgga    600
acaggggacg ttataacacc ccctaagggt gcaaagatc tatttaaaaa gcttaaagtt    660
gaagacaaag agctgaaaga gtttccagga gcctatcacg agatatttga ggatcctgag    720
tggggcgagg agtttcacaa aaccatagtg gagtggcttt tgcagcattc cgaggagggt    780
tga                                                                  783
```

<210> SEQ ID NO 3
<211> LENGTH: 256
<212> TYPE: PRT
<213> ORGANISM: Pyrococcus

<400> SEQUENCE: 3

Met Ile Phe Lys Ala Lys Phe Gly Glu Pro Lys Arg Gly Trp Val Val
1               5                   10                  15

Ile Val His Gly Leu Gly Glu His Ser Gly Arg Tyr Ala Lys Leu Val
            20                  25                  30

Glu Met Leu Val Glu Arg Gly Phe Ala Val Tyr Thr Phe Asp Trp Pro
        35                  40                  45

Gly His Gly Lys Ser Ser Gly Lys Arg Gly His Thr Ser Val Glu Glu
    50                  55                  60

Ala Met Glu Ile Ile Asp Glu Ile Ile Glu Ile Gly Glu Lys Pro
65                  70                  75                  80

Phe Leu Phe Gly His Ser Leu Gly Gly Leu Thr Val Ile Arg Tyr Ala
                85                  90                  95

Glu Thr Arg Pro Glu Lys Val Lys Gly Val Ile Ala Ser Ser Pro Ala
            100                 105                 110

Leu Ala Lys Ser Pro Asn Thr Pro Gly Phe Leu Val Ala Leu Ala Lys
        115                 120                 125

Phe Leu Gly Val Val Ala Pro Gly Ile Thr Phe Ser Asn Gly Ile Asn
    130                 135                 140

Pro Asn Leu Leu Ser Arg Asn Lys Asp Ala Val Arg Arg Tyr Val Glu
145                 150                 155                 160

Asp Pro Leu Val His Asp Lys Ile Thr Ala Lys Leu Gly Arg Ser Ile
                165                 170                 175

Phe Met Asn Met Glu Leu Ala His Arg Glu Ala Glu Lys Ile Lys Val
            180                 185                 190

```
Pro Ile Leu Leu Leu Val Gly Thr Gln Asp Val Ile Thr Pro Pro Glu
        195                 200                 205

Gly Ala Arg Lys Leu Phe Glu Lys Leu Lys Val Glu Asp Lys Glu Ile
    210                 215                 220

Arg Glu Phe Glu Gly Ala Tyr His Glu Ile Phe Glu Asp Pro Glu Trp
225                 230                 235                 240

Gly Glu Glu Phe His Arg Val Ile Val Glu Trp Leu Glu Lys His Ser
                245                 250                 255
```

<210> SEQ ID NO 4
<211> LENGTH: 260
<212> TYPE: PRT
<213> ORGANISM: Thermococcus

<400> SEQUENCE: 4

```
Met Glu Val Tyr Lys Val Arg Phe Gly Thr Pro Glu Arg Gly Trp Val
1               5                   10                  15

Val Leu Val His Gly Leu Gly Glu His Ser Gly Arg Tyr Gly Arg Leu
                20                  25                  30

Ile Lys Leu Leu Asn Glu Asn Gly Phe Gly Val Tyr Ala Phe Asp Trp
            35                  40                  45

Pro Gly His Gly Lys Ser Pro Gly Lys Arg Gly His Thr Ser Val Glu
    50                  55                  60

Gly Ala Met Glu Ile Ile Asp Ser Ile Glu Glu Leu Gly Glu Asn
65                  70                  75                  80

Pro Phe Leu Phe Gly His Ser Leu Gly Gly Leu Thr Val Ile Arg Tyr
                85                  90                  95

Ala Glu Ala Arg Pro Asp Lys Ile Arg Gly Val Ile Ala Ser Ser Pro
            100                 105                 110

Ala Leu Ala Lys Ser Pro Glu Thr Pro Asp Phe Met Val Ala Leu Ala
        115                 120                 125

Lys Phe Leu Gly Arg Ile Ala Pro Gly Leu Thr Leu Ser Asn Gly Ile
    130                 135                 140

Lys Pro Glu Leu Leu Ser Arg Asn Arg Asp Ala Val Arg Arg Tyr Val
145                 150                 155                 160

Glu Asp Pro Leu Val His Asp Arg Ile Ser Ala Lys Leu Gly Arg Ser
                165                 170                 175

Ile Phe Val Asn Met Asp Leu Ala His Arg Glu Ala Glu Asn Ile Arg
            180                 185                 190

Val Pro Ile Leu Leu Val Gly Thr Gly Asp Val Ile Thr Pro Pro
    195                 200                 205

Lys Gly Ala Lys Asp Leu Phe Lys Lys Leu Lys Val Glu Asp Lys Glu
210                 215                 220

Leu Lys Glu Phe Pro Gly Ala Tyr His Glu Ile Phe Glu Asp Pro Glu
225                 230                 235                 240

Trp Gly Glu Glu Phe His Lys Thr Ile Val Glu Trp Leu Leu Gln His
                245                 250                 255

Ser Glu Glu Gly
            260
```

<210> SEQ ID NO 5
<211> LENGTH: 9
<212> TYPE: PRT
<213> ORGANISM: Pyrococcus

<400> SEQUENCE: 5

```
Arg Glu Ala Glu Lys Ile Lys Val Pro
1               5

<210> SEQ ID NO 6
<211> LENGTH: 9
<212> TYPE: PRT
<213> ORGANISM: Thermococcus

<400> SEQUENCE: 6

Arg Glu Ala Glu Asn Ile Arg Val Pro
1               5
```

THERMOSTABLE ESTERASES FROM THERMOPHILIC BACTERIA

This application claims priority to European Application No. 03021972.9, filed on Sep. 30, 2003.

FIELD OF THE INVENTION

The present invention relates to newly identified hydrolases from thermophilic microorganisms having thermostable properties, and more specifically, to a novel thermostable hydrolase showing high activity at high temperatures.

BACKGROUND OF THE INVENTION

Hydrolases are well known as biocatalysts. In general, hydrolases can be used in the synthesis or transformation of acyl compounds like esters or amides. The products obtainable by the reactions find a broad spectrum of application. For example, hydrolases are well known for their use in the industrial hydrolysis or transesterification of triglycerides. Other examples are the production of pharmaceuticals or cosmetic ingredients, where stereoselectivity or high quality is of special interest. Production conditions for enzymatic reactions are generally milder and more specific than those of conventional chemical catalysis. Therefore, enzymatic reactions have received considerable and strongly increasing interest.

Industrially used hydrolases have been isolated from a broad variety of organisms, including bacteria, yeasts, higher animals and plants. However, most hydrolases have a limited operational temperature range, and are not suited for operations at increased temperatures.

There are several hydrolases, more specifically esterases, which can be used without deactivation at temperatures of about 60° C.; 70° C. being the absolute temperature maximum. An example is a lipase isolated from *Candida antarctica* which can be supplied in immobilised form. The absolute temperature maximum of this enzyme is 70° C. before the enzyme degradation becomes intolerably strong.

There are, however, numerous raw materials and products in the field of oleochemistry and surfactant chemistry which melt around, or well above, 65° C., e.g., stearic acid at 71° C. and behenic acid at 79° C. For carrying out enzymatic reactions without using solvents, which are generally undesired, and will also considerably increase the production costs, enzymes which are stable well above 60° C. are needed. Another advantage of performing enzymatic reactions at elevated temperatures is the viscosity reducing effect. This is especially useful if oligomers or polymers are converted by enzymatic reactions. In these cases, thermostable enzymes are prerequisites to conduct reactions at increased temperatures. A third aspect highlighting the advantages of thermostable enzymes, which is particularly important in the synthesis of surface active compounds, is reactions of hydrophilic and lipophilic compounds which need to be compatibilized to react with each other. For this purpose, a simple and efficient means is to increase temperature, which requires a suitable enzyme.

For an industrially useful hydrolase biocatalyst, excellent thermostability needs to be accompanied by broad substrate specificity and tolerance against different kinds of substrates and solvents. Indeed versatile catalysts are needed to fulfill the requirement of flexibility, which is essential for multipurpose production units often used in the production of specialty chemicals.

In the last two decades, the discovery and isolation of thermophilic microorganisms, such as eubacteria or archaea, isolated from, e.g., hot springs, or deep-sea hydrothermal vents, has resulted in the identification of new hydrolases which function at temperatures above 60° C. Hydrolases, especially esterases, can be characterized by different substrate specificities, substituent group or chain length preferences, and by unique inhibitors. See, for example, Barman, T. E. Enzyme Handbook, Springer-Verlag, Berlin-Heidelberg, 1969; Dixon, M. et al. Enzymes, Academic Press, New York, 1979. Hydrolases range from carboxylic ester hydrolases such as carboxyl esterases, lipases, phospholipases to peptide hydrolases and proteases. For example, lipases specifically act on long carbon chain substrates such as fats and oils, or generally speaking oleophilic substrates, whereas acylases are specific for short chain derivatives such as $C_2$-$C_6$ esters. Other very specific esterases are cholin esterases, steryl esterases, phospholipases A1 and A2 and many more. In many cases, these hydrolases are also known to show stereo- and regio-selective preferences resulting from the chiral nature inherent to protein active sites.

Hydrolases carry out their natural reactions, e.g., the hydrolysis of ester bonds in aqueous solutions. Under conditions that lack water, the reaction may be reversed and esters are formed from acids and alcohols. In vitro, these enzymes can be used to carry out reactions on a wide variety of substrates, including esters containing cyclic and acyclic alcohols, mono- and diesters, and lactams. See, for example, Santaniello, E., et al., "The biocatalytic approach leads to the preparation of enantiomerically pure chiral building blocks" (Chem. Rev. 92:1071-1140, 1992). By carrying out the reactions in the absence of water, the reactions of hydrolases can go in the reverse direction. The enzymes can catalyze esterification or acylation reactions to form ester or amide bonds (Santaniello, E. et al., supra). This process can also be used in the transesterification of esters, and in ring closure or opening reactions.

Hydrolases are a group of key enzymes in the metabolism of fats and are found in all organisms from microbes to mammals. In hydrolysis reactions, an ester or amide group is hydrolyzed to an organic acid and an alcohol or amine.

There are a number of industrial and scientific applications for hydrolases. In the following, some examples of the numerous uses for hydrolases are listed:

1) Hydrolases in the dairy industry as ripening starters for cheeses, such as the Swiss-type cheeses;
2) Hydrolases in the pulp and paper industry for lignin removal from cellulose pulps, for lignin solubilization by cleaving the ester linkages between aromatic acids and lignin and between lignin and hemicelluloses, and for disruption of cell wall structures when used in combination with xylanase and other xylan-degrading enzymes in biopulping and biobleaching of pulps;
3) Hydrolases in the synthesis of carbohydrate derivatives, such as sugar derivatives;
4) Hydrolases in combination with xylanases and cellulases, in the conversion of lignocellulosic wastes to fermentable sugars for producing a variety of chemicals and fuels;
5) Hydrolases as research reagents in studies on plant cell wall structure, particularly the nature of covalent bonds between lignin and carbohydrate polymers in the cell wall matrix;
6) Hydrolases as research reagents in studies on mechanisms related to disease resistance in plants and the process of organic matter decomposition;
7) Hydrolases in the selection of plant breeds for production of highly digestible animal feeds, particularly for ruminant animals;

8) Lipases in the hydrolysis of fats and oils to produce fatty acids; and
9) Lipases in the transesterification of fats and oils to produce special fats.

The term "hydrolase" as used in this application means that the enzyme belongs to the class E.C.3., according to the Nomenclature Committee of the International Union of Biochemistry and Molecular Biology (NC-IUBMB), as found on www.chem.qmv.ac.uk/iubmb/enzyme/.

Most of the well-known hydrolases on the market, which are used as thermostable lipases or as thermostable hydrolases, are not adequate in stability against heat, and not practical for industrial applications at increased temperatures, broad pH-value ranges, or are not suited for long-term reactions. To date, only one hydrolase and a few lipases have been reported with moderately thermostable characteristics.

Ikeda, M. and D. S. Clark (Biotechnology and Bioengineering, 57, pp. 624-9, 1998) describe the molecular cloning of a thermostable hydrolase gene from the hyperthermophilic archaea *Pyrococcus furiosus* in *E. coli*. However, this document does not disclose the nucleic acid or amino acid sequences of this hydrolase, which functions only optimally in a narrow pH-value range of about 7.6, and shows good activity in a narrow tempera range only, with a temperature optimum at 100° C. Temperature stability could be shown with the following results for the half-life-time: 100° C. 34 h, 110° C. 6 h, 120° C. 2 h and 126° C. 50 min. The enzyme has only low or moderate lipase activity, and is more active to short hydrocarbon chain substrates. The expression of the plasmid containing the hydrolase DNA-sequence was very difficult due to low plasmid stability in liquid cultures of transformed *E. coli*.

Tulin et al. (Biosci. Biotechn. Biochem., 57, pp. 856-857, 1993) reported a hydrolase derived from *Bacillus stearothermophilus* and cloned into *Bacillus brevis*. However, this hydrolase was only stable for up to 10 min at 70° C. Sugihara et al. (J. Biochem., 112, pp. 598-603, 1992) have isolated novel thermostable lipases from two microorganisms, a *Bacillus soil* isolate and a *Pseudomonas cepacia* soil isolate. The former lipase was stable up to 30 min at 65° C., but became rapidly inactivated above this temperature. The lipase from *Pseudomonas cepacia* was stable when heated for 30 min at 75° C. and pH 6.5, but had only 10% of its activity when assayed at this temperature.

Sigurgisladottir et al. (Biotechnol. Lett. 15, pp. 361-366, 1993) reported on the isolation of one *Thermus* stain and two *Bacillus* strains which contain lipases which act on olive oil at temperatures up to 80° C., although there was no report on enzyme stability in this study.

Hotta et al. (Appl. Environ. Microbiol. 68, pp. 3925-3931, 2002) found and characterised a thermostable hydrolase in the archaeon *Pyrobaculum calidifontis*. The hydrolase was shown to be thermostable for at least 2 h at 100° C. and to have a half-life-time at 110° C. of 56 in both measured in aqueous medium. The hydrolase is also fairly stable in the presence of water-miscible organic solvents. Its substrate specificity is limited to short hydrocarbon chain substrates, optimally for $C_6$-chains.

The Japanese Unexamined Patent Publication No. Sho 62-79782 proposed a thermostable lipase. However, the optimum temperature of the enzyme is in the range of 60° C. to 70° C. and its thermostability is poor, since the residual activity after treatment at 70° C. for 15 min is below 10%.

European Patent Publication EP 0 117 553 A1 discloses a thermostable lipase derived from *Rhizopus chinensis*, but the optimum temperature of this enzyme is only 60° C. and the activity at a high temperature is fairly low.

Furthermore, there are reports on a lipase produced by *Pseudomonas mephitica* variety polytica which has an optimum temperature of 70° C. and is not inactivated by heat treatment at 60° C. for 14 h (Japanese Examined Patent Publication No. Sho. 50-25553), and a second lipase produced by *Pseudomonas fraji* which has an optimum temperature in the range of 75° C. to 80° C. and maintains 95% of the activity after heat treatment at 70° C. for 20 min (Agric. Biol. Chem. 41, 1353-1358, 1977). However, the temperature stability of these enzymes does not reach beyond 80° C. for 1 h, and therefore they are not sufficiently satisfactory with regard to thermostability.

U.S. Pat. No. 5,766,912 describes and claims a recombinant *Humicola sp.* lipase having a residual activity of at least 90% after 2 h at 60° C. and a pH from about 6 to about 9, and at least 80% after 2 h at 60° C. and at a pH from about 5.5 to about 9.2. This lipase has a residual activity of at least 95% after 2 h at 55° C. and at a pH from about 6 to about 9.5.

U.S. Pat. No. 5,173,417 describes a thermostable lipoprotein lipase from *Streptomyces*, which exhibits about 100% retention of the hydrolysing activity when treated in a buffer having a pH in the range of about 4 to 7 at about 60° C. for about 15 min, and a glycerol forming activity/fatty acid forming activity ratio of at least about 15%.

U.S. Pat. No. 5,306,636 describes a thermostable lipase from *Pseudomonas sp* KWI-56, which is stable for 24 h at pH 7.0 up to a temperature of 60° C. and which range of adaptable acting temperature with olive oil as the substrate is 60° C. to 65° C., with a pH optimum at 5.5-7.9. However, this lipase is deactivated to an extent of 82% after 24 h at 70° C.

U.S. Pat. No. 5,846,801 describes a thermostable lipase from *Pseudomonas solanacearum* having a temperature optimum of 80-90° C. (determined using triolein emulsion as a substrate), in a pH range of about 4-12, a pH optimum of 6.5-9.5. However, the residual activity of the enzyme had been measured within one hour only. Additionally, *Pseudomonas solanacearum* is a pathogenic microorganism.

U.S. Pat. No. 5,480,787 discloses a transesterification method using lipase powder. Preferably, a commercially available lipase from *Alcaligenes* is used for the transesterification of oils, fats and resins. However, no esterification or hydrolysis reactions are disclosed. Additionally, no disclosure with regard to amide formation by said enzyme is made. Further, the particle diameter of the immobilised hydrolase has to be controlled thoroughly during the enzymatic reactions, else the reactivity is reduced and the recovery of the lipase particles from the reaction liquid is difficult, which makes reuse impossible.

EP 0 709 465 A1 and EP 0 714 984 A1 describe a process for the production of optically active alcohols by a thermostable lipase derived from *Alcaligenes* under water-free conditions without a solvent. These publications, however, do not disclose the use of the lipase for hydrolysis or esterification reactions.

U.S. Pat. No. 5,714,373 discloses *Thermococcus* AV4 and enzymes produced by the same. This publication discloses the identification of a thermostable lipase, which is detected by the lipase activities, such as the hydrolysis of triglycerides to diglycerides and fatty acids, monoglycerides and glycerol. However, no examples for these reactions and no data on thermostability of the lipase are disclosed.

In the light of the prior art, it was desirable to provide hydrolases, and microorganisms producing the same, which combine several advantageous features that are not found in the enzymes of the prior art. Thus, it was necessary to provide a new type of hydrolases that have an excellent thermostability during long time reactions, with a high efficiency in a large pH range, in various media, and that are capable of acting on a broad range of substrates.

SUMMARY OF THE INVENTION

The present invention provides new thermostable hydrolases, useful for reactions involving acyl residues, such as hydrolysis, ester synthesis or amide synthesis, at high temperatures.

The thermostable hydrolases of the present invention can be obtained from archea of the order *Thermococcales*. Preferably, the hydrolases of the present invention can be obtained from the genera *Pyrococcus* or *Thermococcus*.

In one embodiment, the present invention provides a thermostable hydrolase having an amino acid sequence of at least 70% similarity, or preferably, 85% similarity, to one or both of SEQ ID No: 3 and SEQ ID No: 4.

In a preferred embodiment, the thermostable hydrolases of the present invention contain the amino acid motif "EAE". In a particularly preferred embodiment, the "EAE" motif in the hydrolases are directly neighboured by any of the amino acids selected from E, D, Q, N, H, R, and K. In an especially preferred embodiment, the hydrolases of the present invention contain the amino acid motifs REAEKIKVP (SEQ ID No: 5) or REAENIRVP (SEQ ID No: 6).

In a specific embodiment, the thermostable hydrolase according to the present invention has the amino acid sequence as set forth in SEQ ID No: 3, or the amino acid sequence as set forth in SEQ ID No: 4.

The thermostable hydrolases provided by the present invention can be recombinantly produced, and can be repeatedly used. Additionally, the hydrolases can be immobilised on or in a carrier for use in reactions, or can be used as a free hydrolase (i.e., not immobilised).

The thermostable hydrolases provided by the present invention have an activity in catalysing hydrolysis, esterification, transesterification or amide formation reactions over a wide temperature range of 40° C. up to 110° C. Preferably, the hydrolyses have a catalytic activity at temperatures between 60° C. and 105° C., more preferably at temperatures of 80° C.-105° C., even more preferably at temperatures of 90° C.-100° C., and most preferably at a temperature of about 95° C.-100° C.

The thermostable hydrolases of the present invention are stable at a temperature between 85° C.-105° C., over a period of at least 16 h, preferably 24 h, and most preferably 40.

Still further, the hydrolases provided by the present invention shows an activity in a broad range of ph values, i.e. from pH 3 to pH 9, preferably at a pH of 4-8, more preferably at a pH of 4-7, and most preferably at a pH of 5-7. In a particularly preferred embodiment, the hydrolases of the present invention has a pH optimum of pH 6.

Additionally, the hydrolases provided by the present invention are active in a range of solvent conditions, including aqueous, polar and non-polar media, and exhibit an activity for a wide range of substrates having chain lengths from 2-50, preferably 2-24, more preferably 3-18 carbon atoms.

In a further aspect, the present invention provides isolated nucleic acid molecules encoding the hydrolases of the present invention.

In a preferred embodiment, the present invention provides nucleic acid molecules coding for an amino acid sequence as set forth in SEQ ID No: 3 or SEQ ID No: 4, or fragments of SEQ ID No: 3 or SEQ ID No: 4.

In another preferred embodiment, the nucleic acid molecules coding for a hydrolase has a nucleotide sequence as set forth in SEQ ID No: 1 or SEQ ID No: 2, or degenerate sequences of SEQ ID No: 1 or SEQ ID No: 2.

In another embodiment, the present invention provides sequences that are similar to SEQ ID No: 1 or SEQ ID No: 2.

In still another embodiment, the present invention provides variants of the above polynucleotides, which variants encode fragments or derivatives of an enzyme having an amino acid sequence as set forth in SEQ ID No: 3 or SEQ ID No: 4, or an enzyme having an amino acid sequence similar to SEQ ID No: 3 or SEQ ID No: 4.

Moreover, the present invention provides vectors and host cells that contain a nucleic acid molecule described herein. Such vectors and host cells are useful for the recombinant production of the thermostable enzymes of the present invention.

DETAILED DESCRIPTION OF THE INVENTION

Definitions

Figure 1:
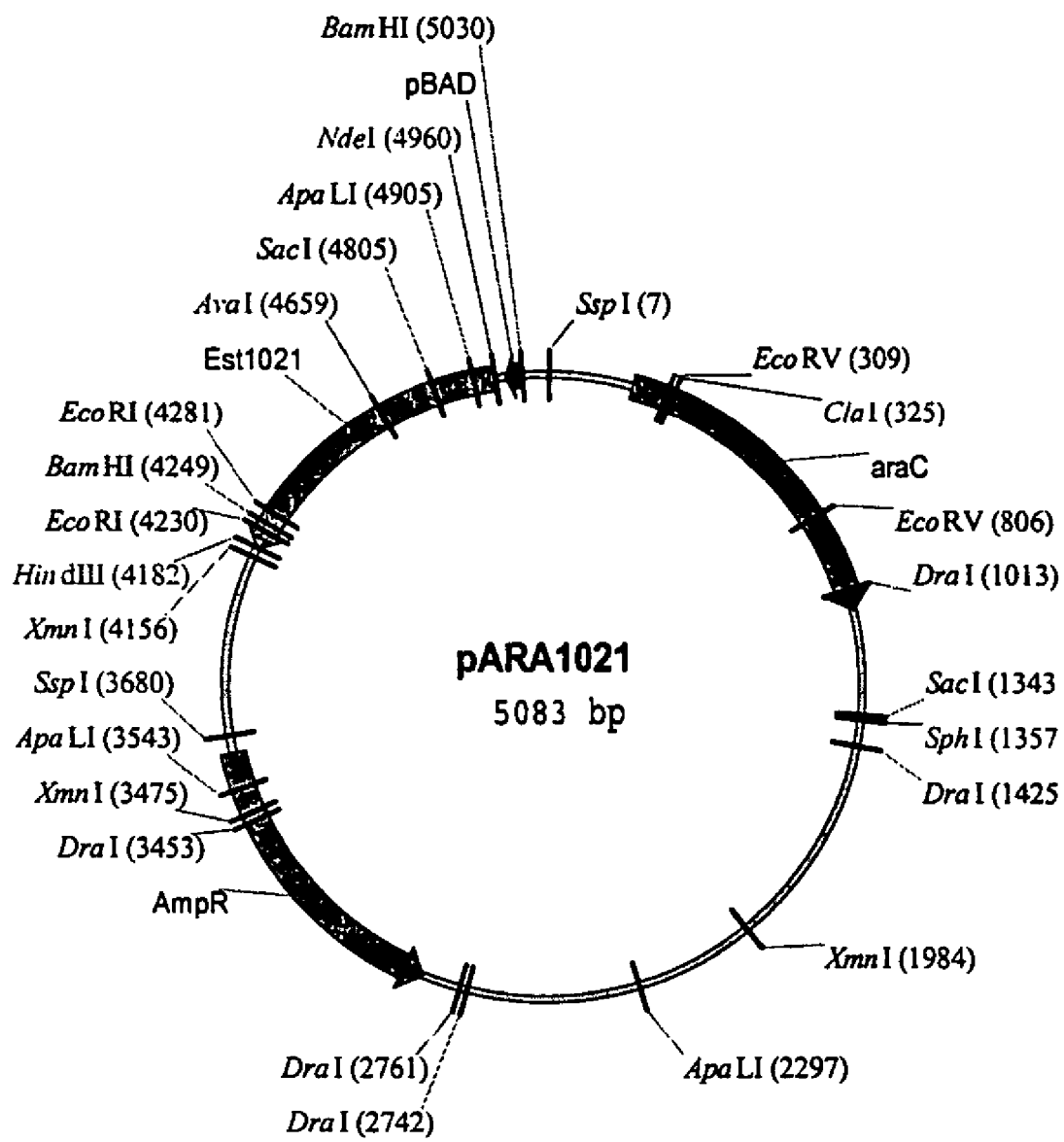
FIG. 1 shows a map of the vector pARA1021 carrying the gene of the invention.

As used herein, the term "thermostable hydrolase" designates a hydrolase having an activity in catalysing hydrolysis, esterification, transesterification or amide formation reactions over a wide temperature range of 40° C. up to 110° C.

Hydrolases of the invention are classified in E.C.3 according to the Nomenclature Committee of the International Union of Biochemistry and Molecular Biology, and encompass enzymes acting on ester-, peptide- and other carbon-nitrogen bonds, such as esterases, lipases, phospholipases, peptidases, proteases, and amidases.

As used in the present patent application, the pH optimum is the pH where the enzyme has an activity of at least 90% of the maximal activity.

As used in the present patent application, the temperature optimum is the temperature in ° C. where the enzyme has an activity of at least 90% of the maximal activity.

As used herein, the activity of a hydrolase is expressed in esterase units (EU). One EU is the amount of enzyme which hydrolyses one micromole of ester per minute. The unit EU can more generally be applied to all types of reactions catalysed by hydrolases, for example, hydrolysis, esterification, transesterification, amidation, transamidation, among others. The activity of a hydrolase expressed in EU is generally different for each reaction type and corresponds to the amount of educt in micromoles transformed within one minute. The specific activity is the activity related to the amount of biocatalyst per weight measured e.g. in milligram.

As used herein, the term "specific activity" is also used for characterisation of the hydrolases of the present invention. For this purpose, the hydrolysis of 2-hydroxy-4-p-nitrophenoxybutyl alkanoate is applied. In particular, the measurement of the specific activity in EU/mg by hydrolysis of 2-hydroxy-4-p-nitrophenoxybutyl decanoate is carried out according to the method of Lagarde, D. et al., Org. Process Res. Dev., 6 (2002) 441 as described in Example 1.1. A specific activity of 100% is defined as 20 EU/mg, as described in Example 6.2 of this application.

The present invention relates to new thermostable hydrolases, classified as EC 3 enzyme according to the Nomenclature Committee of the International Union of Biochemistry and Molecular Biology (NC-IUBMB), with previously unknown nucleic acid and amino acid sequences, having excellent thermostable properties, obtainable from archaea of the order *Thermococcales*, which can generally be used for reactions involving acyl residues, such as hydrolysis, ester synthesis or amide synthesis at high temperatures. Therefore, hydrolases having an EC classification as EC 3.1, EC 3.4 and EC 3.5 are preferred. The classification information is available from Nomenclature Committee of the International Union of Biochemistry and Molecular Biology (NC-IUBMB), which can also be found on www.chem.qmul.ac.uk/iubmb/enzyme/EC3/.

More specifically, the invention relates to a thermostable hydrolase having an amino acid sequence of at least 70% similarity to any of SEQ ID No: 3 and/or SEQ ID No: 4. A preferred thermostable hydrolase of the present invention has an amino acid sequence of at least 70% similarity to SEQ ID No: 3, or has an amino acid sequence of at least 70% similarity to SEQ ID No: 4.

More preferably, the thermostable hydrolase according to the present invention has an amino acid sequence of at least 85% similarity to SEQ ID No: 3, or has an amino acid sequence of at least 85% similarity to SEQ ID No: 4.

Still more preferably, the thermostable hydrolase according to the present invention has the amino acid sequence as set forth in SEQ ID No: 3, or the amino acid sequence as set forth in SEQ ID No: 4.

Most preferably, the thermostable hydrolase consists of the amino acid sequence as depicted in SEQ ID No: 3, or of the amino acid sequence as depicted in SEQ ID No: 4.

Preferably, the hydrolase is obtainable from archaea of the genera *Pyrococcus* or *Thermococcus*.

In another embodiment of the present invention, the thermostable hydrolase according to the present invention is a recombinantly produced hydrolase.

In still another embodiment of the present invention, the thermostable hydrolase according to the present invention can be repeatedly used, i.e., it is used in one reaction, and then reused a second or a further time in the same or different reaction. Such a thermostable hydrolase is designated as recycled hydrolase in the context of the present invention.

In a further embodiment of the present application, the hydrolase according to the present invention is used as a free hydrolase, which means that the hydrolase has not been immobilised on or in a carrier.

In yet another embodiment, the hydrolase of the present application is used as immobilised hydrolase. The hydrolase can be immobilised on or in a carrier substance according to methods known to skilled persons.

Immobilisation is usually advantageous in order to increase the general stability of an enzyme with respect to temperature, pH and other stressing conditions. Immobilisation further facilitates the removal of the enzyme from a reaction mixture for instance by filtration and immobilisation may even enhance productivity of an enzyme.

There are numerous techniques known for immobilisation. Usually they involve the attachment of the enzyme onto a solid support by adsorptive means or also by covalent binding. There are other techniques which use cross-linking of the enzyme in free or in crystalline form. Additionally, confining the enzyme into a restricted area, e.g., entrapment into a solid matrix or a membrane-restricted compartment, is possible and frequently used. Depending on the immobilisation technique, the properties of the biocatalyst such as stability, selectivity, binding properties for substrates, pH and temperature characteristics can be changed.

Cross-linking of enzymes means the attachment of enzyme molecules with other enzyme molecules by covalent bonds, which results in insoluble high-molecular aggregates. See, e.g., S. S. Wong, L-J C. Wong Enzyme Microb. Technol. 14: 866 (1992). The free enzyme molecules can also be cross-linked with other inactive "filler" proteins such as albumins. The most widely used reagent for immobilisation by cross-linking is α,ω-glutardialdehyde. See, e.g., S. S. Khan, A. M. Siddiqui Biotechnol. Bioeng. 27:415 (1985). This reagent can be used in combination with other cross-linkers like polyazetidine. The advantage of this method is its simplicity.

This invention further relates to a thermostable hydrolase having an activity in catalysing hydrolysis, esterification, transesterification or amide formation reactions over a wide temperature range of 40° C. up to 110° C., preferably at temperatures between 60° C. and 105° C., more preferably at temperatures of 80° C.-105° C., even more preferably at temperatures of 90° C.-100° C., and most preferably at a temperature of about 95° C.-100° C.

The thermostable hydrolase according to the present invention has an optimum temperature range higher than 50° C., preferably in a temperature range of 60° C.-100° C., more preferably in a range of 80° C.-100° C., still more preferably in a range of 90° C.-100° C., and most preferably the temperature optimum is 95° C., as measured by the hydrolysis of 2-hydroxy-4-p-nitrophenoxy-butyl decanoate.

As used herein, temperature stability means that the free enzyme retains at least 15%, preferably 25%, most preferably 35% of its hydrolase activity at a temperature higher than 60° C., preferably 70° C.-115° C., more preferably 80° C.-110° C., and most preferably the enzyme is stable at a temperature between 85° C.-105° C., over a period of at least 16 hours (h), preferably 24 h and most preferably 40 h as measured by the hydrolysis of 2-hydroxy-4-p-nitrophenoxy-butyl decanoate.

Still further, the free hydrolase according to the present invention shows an activity in a broad range of pH values, i.e. from pH 3 to pH 9, preferably at a pH of 4-8, more preferably at a pH of 4-7, most preferably at a pH of 5-7, as determined by the hydrolysis of 2-hydroxy-4-p-nitrophenoxy-butyl decanoate. In a particularly preferred embodiment, the hydrolase of the present invention has a pH optimum of pH 6, i.e. the hydrolase has 50%-100% relative hydrolase activity, preferably 75%-100% relative activity, and most preferably 90%-100% relative activity at pH 6, as measured by the hydrolysis of 2-hydroxy-4-p-nitrophenoxy-butyl-decanoate.

Additionally, the free hydrolase according to the present invention maintains its activity in a range of solvent conditions, including aqueous, polar and non-polar media.

Preferably the hydrolase according to the present invention has a residual activity of at least 30% after heat treatment at 90° C. for 30 min, more preferably at least 40%, most preferably at least 50%, in aqueous or polar or non-polar organic media like alcohols, ketones, esters, carboxylic acids, aliphatic and aromatic hydrocarbons or mixtures thereof. Examples of organic media are ethanol, isopropanol tert-butanol, ethyleneglycol, acetone, cyclohexane, ethyl acetate, ethylene glycol dihydroxystearate, methylcyclohexane, or toluene.

The hydrolase of the present invention is suitable to be used as catalyst in the synthesis of esters, amides or other acyl compounds, and shows very good stability in the corresponding reaction media which may consist of, for example, alcohols and carboxylic acids, alcohols and esters, carboxylic acids and esters, esters and alkylamines.

In a preferred embodiment of the present invention, the hydrolase is an esterase, a lipase, a carboxyesterase, an amidase or a transamidase. The Medical Search Engine at www-.books.md gives the following definitions for the above-mentioned types of hydrolase:

Esterases catalyse the hydrolysis of organic esters to release an alcohol or thiol and acid. The term could be applied to enzymes that hydrolyse carboxylate, phosphate and sulphate esters, but is more often restricted to the first class of substrate.

Lipases hydrolyse fats (mono-, di- or triglycerides) to glycerol and fatty acids.

Carboxyesterases catalyse the hydrolysis of carboxylic acid esters to yield an alcohol and carboxylic acid anion.

Amidases catalyse the hydrolysis of monocarboxylic acid amides to free acid and $NH_3$.

Transamidases catalyse the transfer of $NH_2$ from an amide moiety to another molecule.

In addition, the hydrolase according to the present invention exhibits an activity for a wide range of substrates having chain lengths from 2-50, preferably 2-24, more preferably 3-18 carbon atoms.

Particularly, the hydrolase according to the present invention has a hydrolytic activity of 20-100 EU/mg, as measured by hydrolysis of 2-hydroxy-4-p-nitrophenoxybutyl decanoate at pH 5-7 and 80° C.-100° C.

Moreover, the hydrolase according to the present invention has an esterification activity in the reaction of octanol and lauric acid to octyl laurate at 80° C.-100° C. of 20-100 EU/mg.

Furthermore, the present invention provides an isolated nucleic acid molecule encoding the enzyme of the present invention, and also provides similar sequences.

In a preferred embodiment, the nucleotide sequence of the present invention codes for any of the amino acid sequences according to SEQ ID Nos: 3 or 4, or fragments thereof.

In another preferred embodiment, the nucleotide sequence of the present invention is as depicted in SEQ ID No: 1 or SEQ ID No: 2, or is a degenerated sequence of SEQ ID No: 1 or SEQ ID No: 2.

In the context of the present invention the term "similarity", when referring to nucleic acids, is used to define how closely related two or more separate strands of nucleic acids are to each other.

Isolated nucleic acid sequences encompassed by the present invention are similar if.

a) they are capable of hybridising under conditions hereinafter described, to polynucleotides which are complementary to SEQ ID Nos: 1 or 2 encoding a protein comprising an amino acid sequence as depicted in SEQ ID Nos: 3 or 4, and if the encoded protein retains at least 80%, preferably 90% of its original specific activity.

b) they are degenerated variants of the polynucleotides of SEQ ID Nos: 1 or 2, and if the encoded protein retains at least 80%, preferably 90% of its original activity of a hydrolase.

The DNA sequences of SEQ ID Nos: 1 and 2 encode the amino acid sequences of SEQ ID Nos: 3 and 4, respectively. Degenerated DNA sequences of SEQ ID Nos: 1 and 2 having variations in the nucleotide coding sequences also fall under the scope of the invention if they encode an amino acid sequence according to SEQ ID No: 3 or 4. Moreover, sequences which are similar to SEQ ID No: 1 or SEQ ID No: 2 are also encompassed by the scope of this invention. These similar sequences can have from 1-30 nucleotide exchanges, preferably 1-10 exchanges, preferably without altering the encoded amino acid motif "EAE" as described below, and preferably the encoded protein retains at least 80%, preferably 90% of the original specific activity of the proteins encoded by SEQ ID Nos: 1 or 2. The nucleotide sequences that are similar can be identified by hybridisation or by sequence comparison.

A means for isolating a nucleic acid molecule encoding an enzyme of the present invention is to probe a gene library with a natural or artificially designed probe using art recognised procedures (see, for example: Current Protocols in Molecular Biology, Ausubel F. M. et al., (EDS) Green Publishing Company Assoc. and John Wiley Interscience, New York, 1989, 1992), wherein the probe is complementary to either SEQ ID Nos: 1 or 2, and the identified nucleic acid has at least 90%, preferably 91%-97% similarity to SEQ ID No: 1 or SEQ ID No: 2. It is appreciated by one skilled in the art that the polynucleotides complementary to SEQ ID No: 1 or SEQ ID No: 2, or fragments of SEQ ID No: 1 or 2 that are coding for amino acid sequences which encompass the amino acid motif "EAE", and which retain at least 80%, preferably 90% of the original specific activity of the encoded protein, are particularly useful probes.

With respect to nucleic acid sequences which hybridise to the specific nucleic acid sequences disclosed herein, hybridisation can be carried out under conditions of reduced stringency, medium stringency or even stringent conditions. As an example of stringent oligonucleotide hybridisation, a polymer membrane containing immobilised denatured nucleic acids is first prehybridized for 30 min at 45° C. in a solution of 0.9 M NaCl, 50 mM $NaH_2PO_4$, pH 7.0, 5.0 mM $Na_2EDTA$, 0.5% SDS, 10×Denhardt's, and 0.5 mg/ml polyriboadenylic acid. Approximately $2\times10^7$ cpm (specific activity $4-9\times10^8$ cpm/μg) of $^{32}P$ end-labelled oligonucleotide probe are then added to the solution. After 12-16 h of incubation, the membrane is washed for 30 min at room temperature in 1×STE (150 mM NaCl, 20 mM Trishydrochloride, pH 7.8, 1 mM $Na_2$ EDTA) containing 0.5% SDS, followed by a 30 min wash in fresh 1×STE at Tm−10° C. for the oligonucleotide probe. The membrane is then exposed to auto-radiographic film for detection of hybridisation signals.

The term "stringent conditions" means that hybridisation will occur only if there is at least 90% similarity, preferably at least 95% similarity and most preferably at least 97% similarity between the sequence of SEQ ID No: 1 or SEQ ID No: 2 and the sequence identified by hybridisation (see J. Sambrook et al., Molecular Cloning, A Laboratory Manual, $2^{nd}$ Ed., Cold Spring Harbour Laboratory, 1989).

As used herein, a DNA (RNA) sequence is at least 50%, or at least 60%, or at least 70%, preferably 80%, more preferably 90%, even more preferably at least 95% and most preferably at least 97% similar to another DNA (RNA) sequence, if there is such similarity between the bases of the one sequence and the bases of the other sequence, when properly aligned with each other. For this purpose any align program can be used, for example BLASTIN®.

The present invention further relates to a degenerate polynucleotide which differs from the reference polynucleotide by changes are silent changes, i.e., changes that do not alter the amino acid sequence encoded by the polynucleotide. The present invention also relates to nucleotide changes which result in amino acid substitutions, additions, deletions, fusions and truncations in the polypeptide encoded by the reference polynucleotide. In a preferred aspect of the invention, these polypeptides retain the same biological activity as the polypeptide encoded by the reference polynucleotide, however they should retain at least 90% of the biological activity of the natural polypeptide.

The polynucleotide of the present invention can be in the form of RNA or DNA, which DNA includes cDNA, genomic DNA, and synthetic DNA. The DNA can be double-stranded or single-stranded, and if single stranded can be the coding strand or non-coding (anti-sense) strand.

The coding sequence which encodes the enzyme can be identical to the coding sequences shown in SEQ ID Nos: 1 and 2, or may have a different coding sequence, however, the coding sequence encodes the same enzyme as the DNA of SEQ ID Nos: 1 and 2 as a result of the redundancy or degeneracy of the genetic code.

The polynucleotide which encodes the enzyme of SEQ ID Nos: 1 and 2, and sequences similar thereto can include, but is not limited to, the coding sequences for the enzyme; the coding sequence for the enzyme and additional coding sequence such as a leader sequence or a pro-protein sequence; the coding sequence for the enzyme (and optionally additional coding sequences) and non-coding sequences, such as introns or non-coding sequences 5' and/or 3' of the coding sequence for the enzyme.

Thus, the term "polynucleotide encoding an enzyme (protein)" encompasses polynucleotides which include only coding sequences for the enzyme as well as polynucleotides which include additional coding and/or non coding sequences.

The present invention further relates to variants of the hereinabove described polynucleotides, which variants encode fragments and derivatives of the enzyme having the deduced amino acid sequences of SEQ ID Nos: 3 and 4, and of amino acids sequences similar to SEQ ID Nos: 3 or 4. The variants of the polynucleotides can be naturally occurring allelic variants of the polynucleotides or non-naturally occurring variants of the polynucleotide.

Thus, the present invention includes polynucleotides encoding the same enzymes as shown in SEQ ID Nos: 3 and 4, as well as variants of such polynucleotides, which variants encode for fragments, derivatives or analogues of the enzymes. Such nucleotide variants include deletion variants, substitution variants and addition or insertion variants.

As hereinabove indicated, the polynucleotides can have coding sequences which are naturally occurring allelic variants of the coding sequences shown in SEQ ID Nos: 1 and 2. As known in the art, an allelic variant is an alternate form of a polynucleotide sequence which may have a substitution, deletion or addition of one or more nucleotides, which does not substantially alter the function of the encoded enzyme, i.e. at least 80%, preferably 90% of the activity of the natural enzyme is preserved.

Fragments of a full-length gene of the present invention can be used as hybridisation probes for screening a cDNA or a genomic library to isolate the full length DNA and to isolate other DNAs which have a high sequence similarity to the gene or similar biological activity. Probes of this type preferably have at least 10, more preferably at least 15, and even more preferably at least 30 bases and can contain, for example, at least 50 or more bases. The probe can also be used to identify a DNA clone corresponding to a full length transcript and a genomic clone or clones that contain the complete gene including regulatory and promoter regions, exons and introns. An example of a screen comprises isolating the coding region of the gene by using the known DNA sequence to synthesise an oligonucleotide probe. Labelled oligonucleotides having a sequence complementary to that of the genes of the present invention are used to screen a library of genomic DNA to determine which members of the library the probe hybridises to.

It is also appreciated that such probes can be and are preferably labelled with an analytically detectable reagent to facilitate identification of the probe. Useful reagents include but are not limited to radioactivity, fluorescent dyes or enzymes capable of catalysing the formation of a detectable product. The probes are thus useful to isolate complementary copies of DNA from other sources, or to screen such sources for related sequences.

The present invention further relates to polynucleotides which hybridise to any of the hereinabove-described sequences, if there is at least 50%, or at least 60%, or at least 70%, preferably 80%, more preferably 90%, even more preferably at least 95% and most preferably at least 97% similarity between the sequences. The present invention particularly relates to polynucleotides which hybridise under stringent conditions to any of the hereinabove-described polynucleotides. In a preferred embodiment, the polynucleotides which hybridise to any of the hereinabove described polynucleotides encode enzymes which either retain substantially the same biological function or activity as the enzymes encoded by the DNA of SEQ ID Nos: 1 and 2, i.e. at least 80%, preferably 90% of the activity of the natural enzymes.

Alternatively, polynucleotides also encompassed by the present invention can have at least 15 bases, preferably at least 30 bases, and more preferably at least 50 bases which hybridise to any part of a polynucleotide of the present invention. For example, such polynucleotides can be employed as probes for the polynucleotide of SEQ ID Nos: 1 and 2, for example, for recovery of the polynucleotides or as a diagnostic probe or as a PCR primer.

Thus, the present invention is directed to a polynucleotide having at least a 50%, or at least 60%, or at least 70%, preferably 80%, more preferably 90%, even more preferably at least 95%, and most preferably at least 97% similarity to a polynucleotide which encodes the enzymes of SEQ ID Nos: 3 and 4, as well as fragments of the polynucleotides, wherein the fragments have at least 15 bases, preferably at least 30 bases, and most preferably at least 50 bases, which fragments are at least 90% complementary, preferably at least 95% complementary, and most preferably at least 97% complementary under stringent conditions to any portion of the polynucleotide of the present invention.

In a preferred embodiment of the present invention, the thermostable hydrolase has an amino acid sequence having at least 70% similarity to any of SEQ ID No: 3 or SEQ ID No: 4.

The present invention further relates to an enzyme which has the deduced amino acid sequence of SEQ ID Nos: 3 or 4, and in alternative embodiments, to fragments, analogues and derivatives of such enzymes.

In one alternative embodiment, the terms "fragment", "analogue" and "derivative" used when referring to the enzyme of SEQ ID Nos: 3 or 4, designate enzymes which retain essentially the same biological function or at least 80%, preferably 90% activity as such enzymes. Thus, an analogue includes a pro-protein which can be activated by cleavage of the pro-protein portion to produce an active enzyme.

In a further alternative embodiment, the enzyme of the present invention can be a native or recombinant enzyme, preferably a recombinant enzyme.

A still further alternative embodiment designates fragments, derivatives or analogues of the enzyme of SEQ ID Nos: 3 or 4 wherein one or more, e.g. 1-20, preferably 1-10 of the amino acid residues can be substituted with a conserved or non-conserved amino acid residue preferably a conserved amino acid residue), and such substituted amino acid residue may or may not be one encoded by the genetic code, or one in which one or more of the amino acid residues includes a substituent group, or one, in which the enzyme is fused with another compound, such as a compound to increase the half-life of the enzyme (for example, polyethylene glycol), or one in which the additional amino acids are fused to the enzyme, such as a leader or secretory sequence or a sequence which is employed for purification of the enzyme or a pro-protein sequence.

In the present invention, the amino acids are either abbreviated by the standard single letter code, or by their three-letter-code, i.e.

| A | Alanine | (ALA) |
|---|---|---|
| B | Asparagine or Aspartic acid | (Asx) |
| C | Cysteine | (Cys) |
| D | Aspartic acid | (Asp) |
| E | Glutamic acid | (Glu) |
| F | Phenylalanine | (Phe) |
| G | Glycine | (Gly) |
| H | Histidine | (His) |
| I | Isoleucine | (Ile) |
| K | Lysine | (Lys) |
| L | Leucine | (Leu) |
| M | Methionine | (Met) |
| N | Asparagine | (Asn) |
| P | Proline | (Pro) |
| Q | Glutamine | (Gln) |
| R | Arginine | (Arg) |
| S | Serine | (Ser) |
| T | Threonine | (Thr) |
| V | Valine | (Val) |
| W | Tryptophane | (Trp) |
| Y | Tyrosine | (Tyr) |
| Z | Glutamine or Glutamic acid | (Glx) |

The enzyme and polynucleotide of the present invention is preferably provided in isolated form, and is preferably purified to homogeneity. The tern "isolated" means that the material is removed from its original environment (e.g., the natural environment where it is naturally occurring). For example, a naturally-occurring polynucleotide or enzyme present in a living animal is not isolated, but the same polynucleotide or enzyme, separated from some or all of the coexisting materials in the natural system, is isolated. Such polynucleotides or enzymes could be part of a composition and still be isolated in that such vector or composition is not part of its natural environment.

In the literature the terms "similarity" and "homology" are often used interchangeably when amino acid sequences are concerned. But by definition (IUBMB-IUPAC Joint Commission on Biochemical Nomenclature (JCBN) and Nomenclature Committee of the International Union of Biochemistry and Molecular Biology (NC-IUBMB), Newsletter 1989 published among other in Eur. J. Biochem., 1989, 183, pp. 1-4.) two sequences are "homologous" if they share a common evolutionary history, or in other words, if there existed an ancestral molecule in the past that was ancestral to both of the sequences. "Similarity" is a quantity that indicates the percentage of identical amino acids or amino acids with similar properties between two sequences. Two homologous sequences are similar due to their common origin; similar sequences are not necessarily homologous (Gibas C, Jambeck P., Einführung in die praktische Bioinformatik, O'Reilly, Köln, 2002, 1$^{st}$ edition, pp. 185).

As used herein, "conservative" or "non-conservative" mutations refer to replacements of one amino acid residue by another amino acid residue which do not change the enzyme function.

As used herein, the term "identity" refers to the extent to which two amino acid sequences or nucleic acid sequences are invariant. In other words "identity" is the percentage of amino acids or nucleotides that are unchanged between two aligned sequences.

Under the term "alignment" one generally understands the process of lining up two or more sequences to achieve maximal levels of identity (and conservation, in the case of amino acid sequences) for the purpose of assessing the degree of similarity, and the possibility of homology.

In a so-called global alignment, an attempt is made to align the entire sequences, with as many characters (i.e. single amino acid residues for polypeptides, and single nucleotides for polynucleotides) as possible. In a local alignment, by contrast, stretches of a sequence with the highest density of matches are given the highest priority, thus generating one or more—sometimes short—islands of matches in the aligned sequences.

When sequences are aligned, normally the sequence of interest is compared to sequences in a database. The sequence of interest may also be aligned with an incomplete sequence. In that case, the computer program aligns the amino acids in the best possible way.

Sequence alignments and determination of percentage of similarity can be realised by importing a family of amino acid sequence data into the sequence editor seaView (Galtier, N., Gouy, M., and Gautier, C.; CABIOS 12, pp. 543-548, 1996). All sequences are manually aligned to minimise the number of gaps and to unambiguously compare different similar domains of the sequences. This optimised alignment can then be imported into a phylogenetic program (PhyloWin) which permits determination of the percentage of similarity between different sequences and which is applied for the determination of the degree of similarity given in this application.

A phylogenetic program based on proteic distances and PAM distance was used to calculate the phylogenetic distances between the different sequences. The distance between two sequences could be converted into percentage of similarity by the formula $(1-d) \cdot 100$. In this study the fully aligned sequences were used for the analysis.

The enzyme of the present invention includes the enzymes of SEQ ID Nos: 3 and 4, as well as enzymes which have at least 70%, preferably 75%, more preferably 80%, even more preferably 85%, still more preferably 90% similarity, and even more preferably at least 95%, but most preferably 99% similarity to the enzyme of SEQ ID Nos: 3 and/or 4, and also include fragments of such enzymes with such portion of the enzyme generally containing at least 5, 10, 15, 20, 25, 30, 35, 40 amino acids and more preferably at least 50, still more preferred at least 100 amino acids. Also preferred are sequences which have 70%, preferably 75%, more preferably 80%, even more preferably 85%, still more preferably 90%, and most preferably at least 95% identity with the enzyme of SEQ ID Nos: 3 or 4. In the present invention, those sequences which may be aligned as shown for the nucleotide sequences SEQ ID Nos: 1 and 2 are preferred. Most preferred is the nucleotide sequence as schematically represented by SEQ ID No: 1 in the above discussed figure.

A variant, i.e. a "fragment", or "derivative" polypeptide, and reference polypeptide can differ in amino acid sequence by maximally 10%, preferably maximally by 5% or less substitutions, additions, deletions, fusions and truncations, wherein the above alterations can be present in any combination.

Among preferred variants are those that vary from a reference by any amino acid substitution which does not change the enzyme function. These substitutions can be conservative or non-conservative. Typically seen as conservative substitutions are the replacements, one for another, among the aliphatic amino acids Ala, Val, Leu and Ile; interchange of the hydroxyl residues Ser and Thr, exchange of the acidic residues Asp and Glu, substitution between the amide residues Asn and Ghn, exchange of the basic residues Lys and Arg and replacements among the aromatic residues Phe, Tyr.

Most highly preferred are variants which retain the same biological function and activity as the reference polypeptide from which it varies, and at least 80%, preferably 90% of the activity of the natural polypeptide.

Fragments or portions of the enzymes of the present invention can be employed for producing the corresponding full-length enzymes by peptide synthesis; therefore, the figments can be employed as intermediates for producing the full-length enzymes. Fragments or portions of the polynucleotides of the present invention can be used to synthesise the full-length polynucleotides of the present invention.

The hydrolase according to the present invention preferably has an amino acid sequence according to SEQ ID Nos: 3 or 4, encompassing the amino acid motif "EAE". The term "amino acid motif" as used in this context means a fixed sequence of amino acids which is not interrupted by any other amino acid.

Still more preferred hydrolase of the present invention has an amino acid sequence according to SEQ ID Nos: 3 or 4 wherein the amino acids "EAE" are directly neighboured by any of the amino acids selected from the group 1 according to the international nomenclature, i.e. E, D, Q, N, H, R, K at the N-terminal and/or C-terminal ends of the "EAE"-motif. In this context, the term "directly neighboured" means that the above amino acids directly precede or follow said amino acid motif, for example, "EEAE" or "EAEK".

Even more preferred hydrolase of the present invention has an amino acid sequence according to SEQ ID Nos: 3 and 4, encompassing the amino acid motifs REAEKIKVP (SEQ ID No: 5) or REAENIRVP (SEQ ID No: 6) and has hydrolase activity.

The hydrolase of the present invention moreover relates to amino acid sequences of hydrolases having at least 85% similarity with SEQ ID Nos: 3 or 4 provided that the amino acid motif "EAE" is preserved.

Preferably, the amino acid sequences of the present invention are derived from microorganisms, for example an archaea. Still more preferably, the amino acid sequences SEQ ID Nos: 3 and 4, as well as the polynucleotides as depicted in SEQ ID Nos: 1 and 2 of the hydrolases according to the present invention are derived from microorganisms of the genera *Pyrococcus* or *Thermococcus*, and most preferred from the species containing the amino acid sequence SEQ ID No: 3.

The present invention also relates to vectors which include polynucleotides of the present invention, host cells which are genetically engineered with vectors of the invention and the production of enzymes of the invention by recombinant techniques.

Host cells are genetically engineered (transduced or transformed or transfected) with the vectors of this invention which can be, for example, a cloning vector or an expression vector. The vector can be, for example, in the form of a plasmid, a viral particle, a phage, etc. The engineered host cells can be cultured in conventional nutrient media modified as appropriate for activating promoters, selecting transformants or amplifying the genes of the present invention.

The culture conditions, such as temperature, pH and the like, are those previously used with the host cell selected for expression, and will be apparent to the ordinarily skilled person.

The polynucleotide of the present invention can be employed for producing enzymes by recombinant techniques. Thus, for example, the polynucleotide can be included in any one of a variety of expression vectors for expressing an enzyme. Such vectors include chromosomal, non-chromosomal and synthetic DNA sequences, e.g. derivatives of SV40, bacterial plasmids, phase DNA, baculovirus, yeast plasmids, vectors derived from combinations of plasmids and phase DNA, viral DNA such as vaccinia, adenovirus, fowl pox virus, and pseudorabies. However, any other vector may be used as long as it is replicable in the host.

The appropriate DNA sequence can be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (e.g., promoter) to direct mRNA synthesis. Representative examples of promoters include LTR or SV40 promoter, the *E. coli* lac or trp, the phase lambda PL promoter, and other promoters known to control expression of genes in prokaryotic or eukaryotic cells or their viruses. The expression vector can also contain a ribosome binding site for translation initiation and a transcription terminator. Additionally, the vector can include appropriate sequences for amplifying expression.

In addition, the expression vectors preferably contain one or more selectable marker genes to provide a phenotypic trait for selection of transformed host cells, for example, dihydrofolate reductase or neomycin resistance for eukaryotic cell culture, or tetracycline or ampicillin resistance in *E. coli*.

The vector containing the appropriate DNA sequence as hereinabove described, as well as an appropriate promoter or control sequence, can be employed to transform an appropriate host to permit the host to express the protein.

Representative examples of appropriate hosts include, but are not limited to, bacterial cells, such as *E. coli, Streptomyces, Bacillus subtilis*; fungal cells, such as *Aspergillus trichoderma*; yeast, such as *Saccharomyces* or *Pichia*; insect cells such as *Drosophila* S2 and *Spodoptera* Sf9; other animal cells such as CHO, COS or *Bowes melanoma; adenoviruses*; plant cells, among others. The selection of an appropriate host is deemed to be within the scope of those skilled in the art from the teachings herein.

More particularly, the present invention also includes recombinant constructs containing one or more of the sequences as broadly described above. The constructs are generally composed of a vector, such as a plasmid or viral vector, into which a sequence of the invention has been inserted, in a forward or reverse orientation. In a preferred aspect of this embodiment, the construct further contains regulatory sequences, including, for example, a promoter, operably linked to the sequence. Large numbers of suitable vectors and promoters are known to those skilled in the art, and are commercially available. However, any material other than a plasmid or a vector can be used as long as they are replicable in the host.

Promoter regions can be selected from any desired gene using CAT (chloramphenicol transferase) vectors or other vectors with selectable markers. Particularly, bacterial (LacI trp, ara, alk), phagic (T3, T7, PL) or hybrid promoters (Trc, Tac) are suitable examples of promoters. Eukaryotic promoters include CMV immediate early, HSV thymidine kinase, early and late SV40, LTRs from retrovirus and mouse metallothionine-I. Selection of an appropriate vector and promoter is well within the level of ordinary skill in the art.

In a further embodiment, the present invention relates to host cells containing any of the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE—Dextran mediated transfection, or electroporation (Davis, L., Dibner, M., Battey, I., Basic methods in Molecular Biology, 1986).

The constructs in host cells can be used in a conventional manner to produce the gene product encoded by the recombinant sequence. Alternatively, the enzymes of the invention can be synthetically produced by conventional peptide synthesisers.

Proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al. (Molecular Cloning: A Laboratory Manual, Second Edition, Cold Spring Harbour, N.Y., 1989).

Transcription of the DNA encoding the enzymes of the present invention by higher eukaryotes is increased by inserting an enhancer sequence into the vector. Enhancers are cis-acting elements of DNA, usually about from 10 to 300 nucleotides distant from a promoter to increase its transcription. Examples include the SV40 enhancer, a cytomegalovirus early promoter enhancer, the promoter enhancer on the late side of the replication origin, and adenovirus enhancers.

Generally, recombinant expression vectors include origins of replication and selectable markers permitting transformation of the host cell, e.g., the ampicillin resistance gene of *E. coli* and *S. cerevisiae* TRPI gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of a translated enzyme. Optionally, the heterologous sequence can encode a fusion enzyme including an N-terminal identification peptide imparting desired characteristics, e.g., stabilization or simplified purification of an expressed recombinant product.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification. When the enzyme is secreted into the culture medium, cells are normally removed by centrifugation and the supernatant is used for further concentration and purification steps.

Microbial cells employed in expression of proteins can be disrupted by any convenient method, including freezethaw cycling, sonification, mechanical disruption, or use of cell lysing agents, which are well known to those skilled in the art.

Various mammalian cell culture systems can also be employed to express recombinant protein. Examples of mammalian expression systems include the COS-7 lines of monkey kidney fibroblasts, described by Gluzman (Cell, 23, pp. 175, 1981), and other cell lines capable of expressing a compatible vector, for example, the C127, 313, CHO, HeLa and BHK cell lines. Mammalian expression vectors typically contain an origin of replication, a suitable promoter and enhancer, and also any necessary ribosome binding site, polyadenylation site, splice donor and acceptor sites, transcriptional termination sequences, and 5' flanking non-transcribed sequences. DNA sequences derived from the SV40 splice and polyadenylation sites can be used to provide the required non-transcribed genetic elements.

The enzymes can be recovered and purified from recombinant cell cultures by any suitable methods, including ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps can be used, as necessary, in completing configuration of the protein. Finally, high performance liquid chromatography (HPLC) can be employed for final purification steps.

The enzymes of the present invention may be naturally purified products, or products of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the enzymes of the present invention can be glycosylated or non-glycosylated. Enzymes of the invention may or may not also include an initial methionine amino acid residue.

The present invention is further described with reference to the following examples. However, it is to be understood that the present invention is not limited to such examples.

EXAMPLES

Example 1

General Methods for Determination of Esterase Activity 1.1: Hydrolytic Activity

The specific activity of an esterase was expressed in esterase units (EU) per milligram of biocatalyst. One EU is the amount of ester in μmol that is hydrolysed or formed within one minute:

$$\text{specific activity} = \frac{EU}{mg_{biocatalyst}} = \frac{\frac{\mu mol_{reacted\ substrate}}{min}}{mg_{biocatalyst}}$$

The specific activity of the esterase in hydrolysis was measured according to a published method (D. Lagarde, H. K. Nguyen G. Ravot, D. Wahler, J.-L. Reymond, G.

Hills, T. Veit, F. Lefevre, Org. Process Res. Dev., 6, pp. 441, 2002) by monitoring the concentration of p-nitrophenol liberated from 2-hydroxy-4-p-nitrophenoxy-butyl decanoate (C10-HpNPB) at a wavelength of λ=414 nm. The procedure was as follows. All reagents and buffers were prepared in deionized MilliQ® water. A 20 mM stock solution of C10-HpNPB in acetonitrile was prepared. A BSA solution was prepared as a stock solution (50 mg/ml) in water. A $NaIO_4$ solution was freshly prepared as a 100 mM stock solution in water. 8 µl of C10-HpNPB stock solution were added to 74 µl of 200 mM PIPES buffer at pH 7.0. The reaction was initiated by adding 10 µl of the enzyme sample. The reaction mixture was incubated at 90° C. for 40 min. The sample was cooled down on ice and BSA (2 mM), $NaIO_4$, (28 mM) and $Na_2CO_3$ (40 mM) were added to the mixture. After 10 min of incubation at 25° C. the sample was centrifuged at 6000 g for 5 min and transferred to a microplate. The optical density of the yellow p-nitrophenol was recorded at λ=414 nm using a Spectramax 190 microplate spectrophotometer (Molecular Devices).

For relative activity measurements, the absolute activities were set in relation to each other in percent. For measurement of the absolute activity, the procedure was as follows.

With the known extinction coefficient of p-nitrophenol $$(\varepsilon_{414\,nm}^{pH7.0} = 14200 M^{-1} \cdot cm^{-1})$$

the change in p-nitrophenol concentration $\Delta c_{liberated\ p\text{-}nitrophenol}$ was calculated with the law of Lambert-Beer $$\Delta c_{liberated\ p\text{-}nitrophenol} = \frac{\Delta E}{\varepsilon \cdot d}$$

in which d stands for the layer thickness and $\Delta E$ describes the change in extinction. The volumetric activity (vol. activity) is then given by the time-dependent change in concentration of nitrophenol $$\text{vol. activity} = \frac{\Delta c_{liberated\ p\text{-}nitrophenol}}{t_{mon}} \cdot f_d$$

in which $t_{mon}$ stands for the monitoring time and $f_d$ is the dilution coefficient of the enzyme extract. Finally, the specific activity was calculated by dividing the volumetric activity by the concentration $c_{enzyme}$ of the enzyme containing material (e.g. raw extract, immobilised enzyme, pure enzyme)

$$\text{spec. activity} = \frac{\text{vol. activity}}{c_{enzyme}}$$

C10-HpNPB was synthesised from 2-bromo-butene as described for the corresponding fluorescent umbelliferone derivatives (F. Badalassi, D. Wahler, G. Klein, P. Crotti, J.-L. Reymond, Angew. Chem. Int. Ed., 39, pp. 4067, 2000; D. Wahler, F. Badalassi, P. Crotti, J.-L. Reymond, Angew. Chem. Int. Ed., 40, pp. 4457, 2001).

1.2: Esterification Activity

Activity in esterification was measured by determination of conversion by acid value titration. The conversion (t) for a given point of time t was calculated as follows $$\text{conversion}\ (t) = \frac{\text{acid value}\ (t=0) - \text{acid value}\ (t)}{\text{acid value}\ (t=0)}$$

where acid value (t=0) is the initial acid value and acid value (t) is the acid value at a given point of time t. Conversion (t) was plotted against time t and the resulting data points were fitted with the program GraFit (Erithacus Software Ltd., P.O. Box 274, Horley, Surrey, RH6 9YJ, UK) to an adapted Michaelis-Menten equation $$\text{conversion}\ (t) = \text{conversion}_{max} \cdot \frac{t}{const + t}$$

In this equation "$\text{conversion}_{max}$", indicates the maximal conversion and "const" is a variable describing the bending of the curve. Differentiation for t for calculating the initial slope of the measured curve yields $$\frac{d(\text{conversion})}{dt} = \text{conversion}_{max} \cdot \frac{const}{(const + t)^2}$$

Initial specific enzyme activity k was calculated with t=1 min as follows $$k = \frac{\frac{d(\text{conversion})}{dt} \cdot \mu moles_{formed\ ester}}{mass_{biocatalyst}\ (mg)}$$

1.3: Transesterification Activity

Transesterification activity was calculated using the mathematical means described in example 1.2 and by determination of conversion (t) with GC. The reaction mixture was derivatised with N-methyl-N-trimethylsilyltriflour-acetamide (MSTFA) and composition of the sample was determined by using a 30 m 0.32 mm apolar capilar GC column with split injection and FID-detection. Conversion (t) at a given point of time t was calculated as follows $$\text{conversion}\ (t) = \frac{A_{ester}\ (t=0) - A_{ester}\ (t)}{A_{ester}\ (t=0)}$$

In this $A_{ester}(t=0)$ indicates the initial GC area of the educt ester before reaction and $A_{ester}(t)$ represents the GC area of the educt ester at a given point of time t.

Example 2

Production of the Free *Pyrococcus* Esterase SEQ ID No: 3

In the following the esterase is called Est P 1021.

2.1: Culture Medium M21 and Growth Conditions of *Pyrococcus* Strain Est P 1021

The medium M21 containing (L-1) was prepared as follows:

| | |
|---|---|
| Yeast Extract | 2 g |
| Casein enzymatic hydrolysate (Sigma P 1192) | 4 g |
| Sea salts | 30 g |
| Cysteine | 0.5 g |
| PIPES | 6.05 g |
| Resazurine(0.1% w/v) | 1 ml |
| Sulphur | 10 g |

The pH was adjusted to 7.5 with NaOH, the medium was heated to 100° C., cooled and dispensed under $N_2/CO_2$ (80/20). Before use the medium was reduced with 2 ml of a sterile anaerobic solution of $Na_2S.9H_2O$ (2% W/v) for 100 ml of M21 medium.

2.2: Production of Est P 1021 with the Native Strain

For the production of esterase, 4 anaerobic flasks containing 3 L of medium M21 were prepared. Each flask was inoculated with 120 ml of a fresh over-night culture of *Pyrococcus* (P 1021) grown under the conditions described in Example 2.1. After 16 h of incubation at 95° C., the culture was centrifuged at 8000 g for 15 min at 4° C. The supernatant was discarded and the cells were resuspended in 27 ml of fresh M21 medium. The cells were lysed by ultrasonification using an amplitude of ultrasonic vibration at the tip of the horn of 10. 10 cycles of 30 sec with 1 min of pause were used (Sonicator ultrasonic liquid processor XL, Misonix Incorporated). Cell debris was removed by centrifugation and proteins were recovered from the supernatant. Protein concentration was measured according to the Bradford assay calibrated against bovine serum albumin (M. M. Bradford, Anal. Biochem. 72 (1976) 248). The specific activity was determined according to Example 1.1 to be 5-7 mEU/mg with a stock protein concentration of 8.5-12 mg/ml with the following data:

$\Delta E=0.682$; $\epsilon=14200$ $M^{-1}cm^{-1}$; $d=0.2$ cm; $t_{mon}=40$ min; $f_d=10$

Example 3

Cloning of *Pyrococcus* Esterase (Est P 1021)

A genomic library of the strain P 1021 (7000 clones) was constructed and screened at 95° C. using C10-HpNPB substrate as previously reported (D. Lagarde, H. K. Nguyen, G. Ravot, D. Wahler, J.-L. Reymond, G. Hills, T. Veit, F. Lefevre, Org. Process Res. Dev., 6 (2002) 441).

Three different clones showing an esterase activity at 95° C. were sequenced. Each clone showed a common open reading frame of 771 bp encoding for the esterase activity. One of these genomic fragments was directly used for constructing a transformation vector.

Example 4

Construction of the Vector pARA P 1021

The open reading frame identified as the esterase gene P 1021 was subcloned into a pARA 14 based vector (C. Cagnon, V. Valverde, J. M. Masson: Protein Engineering 4, 843, 1991) in which the NcoI cloning site was replaced by a NdeI cloning site. A polymerase chain reaction product of the open reading frame amplified from the genomic DNA of *Pyrococcus* strain P 1021 was obtained using 2 primers carrying a NdeI site in 5' position and a Hind III site in 3' position for the cloning of the esterase gene in the pARA based vector under the control of an arabinose inducible promoter. The map of the resulting vector is shown in FIG. 1.

Example 5

Production of Recombinant EST P 1021 Using the Vector pARA P 1021

The pARA P 1021 vector from Example 4 was used to transform the *E. coli* strain MC 1061 pRIL. A 4 liter Erlenmeyer flask fermentation was run in standard Luria Broth (LB) medium containing 10 g/l bactotryptone, 5 g/l yeast extract and 5 g/l sodium chloride. LB medium was supplemented with 100 mg/l ampicillin and 30 mg/l chloramphenicol. The medium was inoculated with 3% v/v of a preculture at 37° C. and pH 7.0. The culture was incubated under shaking (200 rpm). Expression of the esterase gene was induced by addition of 0.02% (v/v) L-arabinose at an optical density at 600 nm of 0.4. Cells were centrifuged 3 h after induction to a final optical density at 600 nm of 1.9. For lysis cells were resuspended in 0.20 M phosphate buffer of pH 8.0 to give a final volume of 30 ml. The cell suspension was then passed once through a high pressure homogeniser at 2 kbars and debris was removed by centrifugation at 13000 g for 20 min. The stock protein concentration was about 20 to 30 mg/ml. The specific activity of the unpurified recombinant raw esterase was determined according to example 1.1 to be 2-3 EU/mg with the following data:

$\Delta E=0.710$; $\epsilon=14200$ $M^{-1}cm^{-1}$; $d=0.2$ cm; $t_{mon}=40$ min; $f_d=10000$

Example 6

Hydrolytic Activity of Free Purified Esterase Est P 1021

6.1: Purification of the Esterase Est P 1021

For purification, harvested cells from Example 5 were resuspended in a HEPES Buffer (0.1 M HEPES, 0.5% (w/v) CHAPS, pH 7.0) up to an optical density at a wavelength of 600 nm of 120. Cells were lysed by ultrasonification (Branson Sonifier 450/2×30 s at level 10 on ice) and soluble proteins were separated from insoluble parts and cell debris by centrifugation for 20 min at 13000 g. The supernatant was heated at 80° C. for 30 min. A second centrifugation for 20 min at 13000 g separated the precipitated *E. coli* proteins. The clear supernatant was supplied to an equilibrated anion exchange column (POROS 20 HQ, Applied BioSystem, 1.6 ml of gel; equilibration with HEPES buffer consisting of 50 mM HEPES and 0.5% (w/v) CHAPS at pH 8.5). Proteins were eluted at a flow rate of 10 ml/min within 5 min by a salt gradient ranging from 0 to 1M NaCl. Fractions of 1 ml were recovered. Those fractions exhibiting a hydrolytic activity on C10-HpNPB were analysed by SDS polyacrylamide gel electrophoresis (SDS-PAGE) (U. K. Laemmli, Nature, 227, pp. 680, 1970). The fractions were applied to a 15% separation gel and the gel was stained with Coomassie staining solution (0.2% Coomassie, 30% ethanol, 10% acetic acid). Those fractions having at least 90% homogeneity (0.75-0.8 M NaCl) were pooled. The purified esterase showed a band of around 24 kDa on the SDS-PAGE with a concentration of 0.2 mg/ml, as determined by the Bradford assay calibrated against bovine serum albumin (M. M. Bradford, Anal. Biochem., 72, pp. 248, 1976).

6.2: Determination of the Hydrolytic Activity of EST P 1021

The purified esterase was used to determine its hydrolytic activity. Est P 1021 (0.2 mg/ml stock solution from Example 6.1) was mixed in 0.1 M PIPES buffer pH 7.0 with 5 mg/ml of BSA and 1.7 mM of C10-HpNPB. The mixture was incubated 40 min at 90° C. and dropped on ice to stop the reaction. The specific hydrolytic activity was calculated according to Example 1.1 to be 20 EU/mg of protein with the following data:

$\Delta E=0.454$; $\epsilon=14200$ $M^{-1}cm^{-1}$; $d=0.2$ cm; $t_{mon}=40$ min; $f_d=1000$ Example 7

Effect of Temperature on Free Est P 1021 Activity

TABLE 1

| Temperature (° C.) | Relative activity (%) |
|---|---|
| 60 | 46 |
| 70 | 56 |
| 80 | 90 |
| 90 | 96 |
| 95 | 100 |
| 100 | 100 |
| 105 | 93 |

The activity of Est P 1021 was measured by the assay on hydrolytic activity as described in Example 1.1 except that temperature was varied. Incubation of Est P 1021 was done in 0.2 M PIPES buffer at pH 7.0. Results are shown above (Table 1) with an activity at 100° C. taken as 100% for the esterase of the invention.

Example 8

Effect of pH on Free Est P 1021 Activity

The activity of Est P 1021 was measured by the assay on hydrolysis activity as described in Example 1.1 except that the pH was varied by using different aqueous buffers. Results are shown below with an activity at pH 6 taken as 100%.

TABLE 2

| pH | Relative activity (%) |
|---|---|
| 3 | 19 |
| 5 | 61 |

TABLE 2-continued

| pH | Relative activity (%) |
|---|---|
| 6 | 100 |
| 7 | 38 |
| 8.8 | 10 |

Example 9

Thermostability of Free Est P 1021

Samples of culture broth prepared as in Example 5 were heat-treated at 100° C. in aqueous solution buffered with 0.2 M PIPES for variable incubation times. Esterase activity of the heat-treated samples was measured using the hydrolysis assay as described in Example 1.1. The results are expressed as relative activities compared with a not heat-treated control sample and are shown in Table 3.

TABLE 3

| Incubation time (hours) | Residual activity (%) |
|---|---|
| 16 | 32 |
| 23 | 32 |
| 40 | 17 |

Example 10

Solvent Tolerance of Free Est P 1021

2 mg free Est P 1021 were dissolved in 2 ml of an aqueous solution at pH 7.0 buffered with 100 mM. The enzyme was incubated under stirring with isopropanol and ethanol at concentrations of 1 M for 40 min. Then hydrolytic activity of the en was measured according to Example 1.1 and is given as relative activity referred to a control sample without incubation in organic solvents. The results are shown in Table 4.

TABLE 4

| Organic solvent | Residual activity (%) |
|---|---|
| Isopropanol | 40 |
| Ethanol | 80 |

Example 11

Substrate Specificity of Free Est P 1021

TABLE 5

| Substrate | Relative activity (%) |
|---|---|
| C2-HpNPB | 27 |
| C3-HpNPB | 100 |
| C10-HpNPB | 100 |
| C16-HpNPB | 79 |
| C18-HpNPB | 52 |
| C18'-HpNPB | 68 |

The activity of Est P 1021 was measured by the assay on hydrolytic activity as described in Example 1.1 except that instead of only C10-HpNPB also the following substrates were tested in aqueous solution buffered with 0.2 M PIPES:

2-hydroxy-4-p-nitrophenoxy-butyl-acetate (C2-HpNPB),
2-hydroxy-4-p-nitrophenoxy-butyl-propionate (C3-HpNPB),
2-hydroxy-4-p-nitrophenoxy-butyl-palmitate (C16-HpNPB),
2-hydroxy-4-p-nitrophenoxy-butyl-stearate (C18-HpNPB),
2-hydroxy-4-p-nitrophenoxy-butyl-oleate (C18'-HpNPB).

The results are given in Table 5 with the activity for C10-HpNPB taken as 100%.

Example 12

Transesterification of Methyl Laurate with Decanol with Free Est P 1021

535 mg methyl laurate and 395 mg decanol were heated up to 95° C. and 40 mg freeze dried, non-purified Est P 1021 were added. Freeze-drying was achieved by adding 2% (v/v) of PEG dimethylether as a cryoprotector. Reaction conversion referred to methyl laurate was followed by GC as described in Example 1.3 and is shown in Table 6; retention times: 3.5 min (decanol); 5.1 min (methyl laurate); 12.7 min (decyl laurate).

TABLE 6

| Time/minutes | Conversion |
| --- | --- |
| 0 | 0 |
| 960 | 0.048 |
| 2400 | 0.096 |
| 8160 | 0.245 |
| 9600 | 0.272 |

Figure 2:
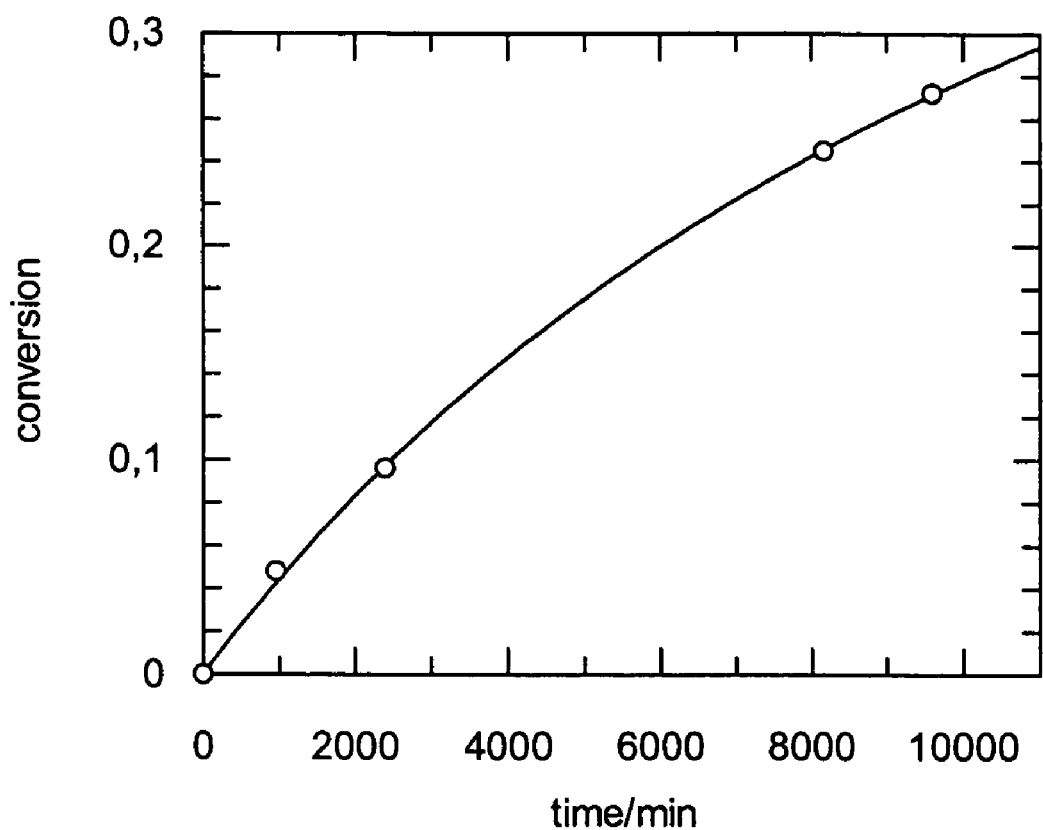
FIG. 2 shows a chart with the transesterification of methyl laurate with decanol with free Est P1021.

The conversion was plotted against time (FIG. 2) and data points were analysed according to Example 1.3. The initial activity k of Est P 1021 in this transesterification was calculated to $$k = 2.9 \frac{mU}{mg}.$$

Example 13

Preparation of Immobilised Recombinant Est P 1021

A culture of recombinant *E. coli* was obtained as described in Example 5. The cells were collected by centrifugation at 6000 g for 15 min. The cells were suspended in 0.25 M Na$_2$HPO$_4$/NaH$_2$PO$_4$ buffer (pH 8.5) to reach roughly 30-40 g/l of dried cells. Cell disruption was performed with a french press afterwards. Cell debris was removed by centrifugation and proteins (concentration 15-30 g/l) were recovered from the supernatant. The pH of the mixture was adjusted to 8-8.5 with 0.25 M of Na$_2$HPO$_4$/NaH$_2$PO$_4$ buffer pH 8.5. 20% of maltitol (w/w) and 10% of glutaraldehyde (w/w) based on the dry weight of the protein were added to the mixture. The suspension was stirred at room temperature for 30 min and 20% of polyazetidine (w/w) based on the dry weight of the protein were added. The reaction mixture was stirred for 15 min at room temperature. The obtained paste was dried overnight at 50° C. The dry pellet was ground to obtain a fine powder.

Example 14

Determination of Activity of Immobilised Recombinant Est P 1021

TABLE 7

| Time/minutes | Conversion |
| --- | --- |
| 0 | 0 |
| 17 | 0.0607 |
| 37 | 0.0401 |
| 124 | 0.0846 |
| 158 | 0.1036 |
| 186 | 0.0849 |
| 236 | 0.0936 |
| 329 | 0.0262 |
| 433 | 0.0432 |
| 1354 | 0.1612 |
| 1530 | 0.1812 |
| 1677 | 0.1836 |
| 1829 | 0.1864 |
| 2866 | 0.2315 |
| 3270 | 0.2480 |
| 4917 | 0.2546 |

Figure 3:
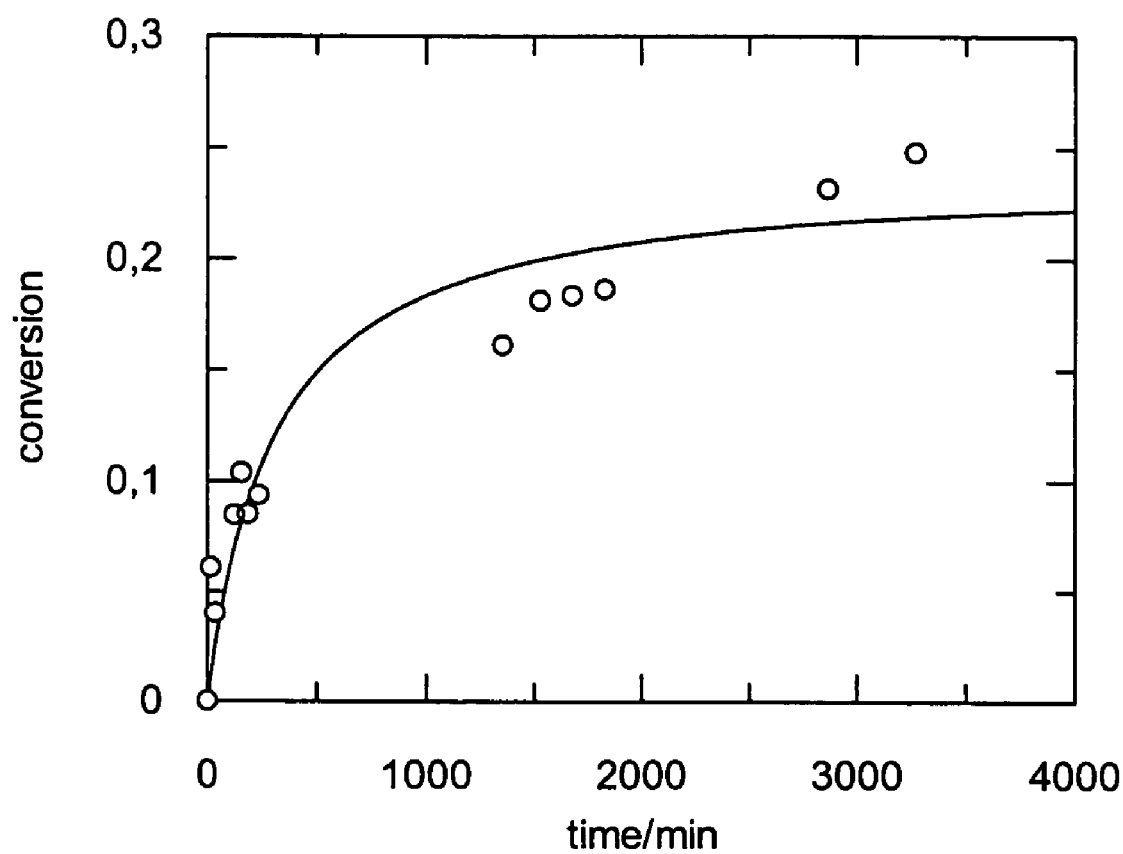
FIG. 3 shows a chart illustrating the determination of the activity of immobilised recombinant Est P1021.

In order to assess the activity of Est P 1021 9.25 g n-propanol and 30.85 g lauric acid were heated up to 60° C. without solvent and 2 g of ground immobilised Est P 1021 prepared as described in Example 13 were added. Acid value was determined by titration with 0.1 N KOH in ethanol to calculate the conversion of the reaction. The results are given in Table 7 and FIG. 3.

Esterase synthesis activity in n-propyl laurate synthesis was calculated analogously to Example 1.2 to be $$k = 60 \frac{mU}{mg}$$

with the following parameters for the adapted Michaelis-Menten equation: conversion$_{max}$=0.24; const=303 min for t=1 min.

Example 15

Effect of Temperature on Activity of Immobilised Est P 1021 in Organic Solvents 4 g ground immobilised Est P 1021 were incubated in 60 ml methylcyclohexane at 95° C. over a period of 450 min to determine the thermostability of the esterase of the present invention. Samples (10 ml) were withdrawn after 123, 248 and 450 min. The solvent was filtered and the remaining enzyme was dried over night at room temperature in an exsiccator at 60 mbar vacuum. The remaining initial en activity was determined analogously to Example 14 in n-propyl laurate synthesis and is given as relative activity compared to the non-treated enzyme in Table 8. No loss of activity was observed over the period of 450 min.

TABLE 8

| Time | Residual activity (%) |
|---|---|
| 123 | 100 |
| 248 | 85 |
| 450 | 90 |

Example 16

Effect of Temperature on Activity of Immobilised Est P 1021 in Water 4 g ground immobilised Est P 1021 were incubated in 60 ml water at 95° C. over a period of 480 min to determine the thermostability of the esterase of the present invention. Samples (10 ml) were withdrawn after 120, 240 and 480 min. The water was filtered and the remaining enzyme was dried over night at room temperature in an exsiccator at 60 mbar vacuum. The remaining initial enzyme activity was determined analogously to example 14 in n-propyl laurate synthesis and is given as relative activity compared to the non-treated enzyme in Table 9. No loss of activity was observed over the period of 480 min.

TABLE 9

| Time | Residual activity (%) |
|---|---|
| 120 | 100 |
| 240 | 115 |
| 480 | 95 |

Example 17

Effect of pH on Immobilised Est P 1021

The specific hydrolytic activity of immobilised Est P 1021 was measured as described in Example 1.1 except that the pH was varied. Results are shown below in Table 10 as relative activities, with activity at pH 6 taken as 100%.

TABLE 10

| pH | Relative activity (%) |
|---|---|
| 3 | 95 |
| 4 | 96 |
| 5 | 93 |
| 6 | 100 |
| 7 | 65 |
| 8.8 | 57 |

Example 18

Thermostability of Immobilised Est P 1021

Est P 1021 powder (2 mg) prepared as described in Example 13 was heat-treated at 90° C. and 100° C. for various incubation times. The specific hydrolytic activity of the heat-treated samples and a control sample without heat-treatment were subsequently measured as described in Example 1.1. Results are shown in Table 11 as relative activities with the activity of the untreated sample taken as 100%.

TABLE 11

| | Residual activity (%) | |
|---|---|---|
| Incubation time (days) | 90° C. | 100° C. |
| 1 | 91 | 80 |
| 2 | 75 | 61 |
| 3 | 55 | 29 |

Example 19

Solvent Tolerance of Immobilised Est P 1021

TABLE 12

| | Residual activity (%) | | | | | |
|---|---|---|---|---|---|---|
| | 1 day | 2 days | 3 days | 5 days | 8 days | 16 days |
| Water | 100 | 100 | 100 | n.d. | n.d. | n.d. |
| 2-Methyl-2-butanol | 68 | 74 | 63 | 60 | 41 | 45 |
| Methylcyclohexane | 66 | 73 | 69 | n.d. | n.d. | n.d. |
| Hydroxystearic acid | 61 | 58 | 61 | n.d. | n.d. | n.d. |

Est P 1021 powder (2 mg) prepared as in Example 13 was heat-treated at 90° C. in the presence of various solvents for different times. Subsequently the solvent was removed by filtration and the esterase powder was washed 3 times with a 0.2 M PIPES buffer at pH 7. The hydrolytic activity of Est P 1021 of the treated samples and a control sample were measured as described in Example 1.1. The results are given in Table 12 as relative activities with the activity of the untreated sample taken as 100%.

Example 20

Esterification of Myristyl Alcohol and Myristic Acid with Immobilised Est P 1021

34.3 g myristic acid and 32.2 g myristyl alcohol were heated to 95° C. and 4 g ground esterase according to the invention was added. Samples (10 g) of the reaction mixture were withdrawn after 1.96, 3.9, and 7.72 days and mixed with 40 g warm acetone, filtered and washed again with 20 g warm acetone twice to remove the ester. After drying over night in an exsiccator under 20 mbar vacuum and ambient temperature, the initial activity was determined analogously to Example 14 and expressed as relative activity compared to the non-treated enzyme. No loss of activity was recognised over this period of 7.72 days (table 13).

TABLE 13

| Reaction time (days) | Residual activity (%) |
|---|---|
| 1.96 | 100 |
| 3.9 | 90 |
| 7.72 | 95 |

Example 21

Repeated Use of the Immobilised Est P 1021 in Myristyl Myristate Synthesis 34.3 g myristic acid and 32.2 g myristyl alcohol were heated up to 95° C. and 4 g ground immobilised esterase as prepared in Example 13 were added. Samples of the reaction mixture were withdrawn after 1, 2, 4, 8 and 24 h for conversion determination by acid value titration. The initial activity in myristyl myristate synthesis was determined by the help of the mathematical means from example 1.2. After 24 h the reaction was stopped and the enzyme was recovered by mixing the ester with 200 g warm acetone, filtering and washing the residual enzyme with 40 g warm acetone twice. After drying the enzyme in an exsiccator over night under 20 mbar vacuum and ambient temperature, the recovered enzyme was used again in myristyl myristate synthesis in the same manner as described above and was shown to maintain its activity following the above described procedure. The procedure was repeated 10 times. The enzyme was stable throughout the entire test, in the last cycle a relative activity of approx. 95% was found which is within the detection limits. The results are shown in Table 14.

TABLE 14

| Reuse No. | Time/min | Conversion | Initial activity/$\left[\frac{mU}{mg}\right]$ |
|---|---|---|---|
| 1 | 0 | 0 | 40 ± 7 |
|  | 30 | 0.052 |  |
|  | 64 | 0.096 |  |
|  | 128 | 0.136 |  |
|  | 246 | 0.194 |  |
|  | 380 | 0.251 |  |
|  | 430 | 0.267 |  |
|  | 1400 | 0.501 |  |
| 10 | 0 | 0 | 42 ± 5 |
|  | 31 | 0.035 |  |
|  | 62 | 0.059 |  |
|  | 124 | 0.105 |  |
|  | 266 | 0.185 |  |
|  | 380 | 0.235 |  |
|  | 450 | 0.271 |  |
|  | 1460 | 0.490 |  |

Example 22

Transesterification of Methyl Laurate and Decanol with Immobilised Est P 1021

23.7 g decanol and 32.2 g methyl laurate were heated up to 95° C. and 1.4 g of ground immobilised Est P 1021 from Example 13 were added. Formed methanol was removed at 300 mbar. After 48 h the reaction was stopped and the catalyst was removed from the reaction mixture by filtration. The composition of the reaction mixture and the conversion was determined with gas chromatography (GC) according to Example 1.3, retention times: 3.5 min (decanol); 5.1 min (methyl laurate); 12.7 min (decyl laurate). The conversion was determined to be 95%.

Example 23

Esterification of Diglycerol and Caprylic Acid with Immobilised Est P 1021

50 g diglycerol and 43.3 g caprylic acid were heated to 95° C. and 3.7 g of ground immobilised Est P 1021 from Example 13 were added. Formed water was removed at 50 mbar. After 48 h the reaction was stopped and the catalyst was removed from the reaction mixture by filtration. The acid value was measured by titration with 0.1 N KOH in ethanol and the conversion was calculated to be 89% referred to caprylic acid.

Example 24

Synthesis of N-stearoyl Stearylamide by Reaction of Methyl Stearate and Stearyl Amine and Immobilised Est P 1021

24.3 g stearyl amine and 26.9 g methyl stearate were heated to 95° C. and 2 g of ground immobilised esterase from example 13 were added. After 48 h at 500 mbar, the reaction was stopped and the catalyst was removed from the reaction mixture by filtration. The composition of the reaction mixture and the conversion referred to methyl stearate was determined to 95% by GC according to Example 1.3. Retention times: 8.6 min (stearyl amine); 9.4 min (methyl stearate); 21.1 min (stearoyl stearyl-amide).

Example 25

Comparative Example of Free Est P 1021, Lipase PL and QL from *Alcaligenes* and Lipase B from *Candida antarctica*

Free enzyme solutions (lipases QL and PL 1 mg/ml; lipase B (state of the art) and Est P 1021 (inventive) 0.01 mg/ml) were heat-treated at 90° C. for variable incubation times in an aqueous solution buffered with 0.2 M PIPES. Specific esterase activity of the heat-treated samples was measured using the hydrolysis assay as described in Example 1.1, except that the assay temperature for lipases QL and PL was set to 40° C. and that for lipase B to 60° C. At these temperatures the highest activities for the not heat-treated enzymes were found. Results are expressed as relative activities compared to the not heat-treated enzymes and are given in Table 15.

TABLE 15

| Incubation time (hours) | Residual activity of lipase QL (%) | Residual activity of lipase PL (%) | Residual activity of lipase B (%) | Residual activity of Est P 1021 (%) |
|---|---|---|---|---|
| 0 | 100.0 | 100.0 | 100.0 | 100.0 |
| 1 | 0.0 | 64.9 | 3.2 | 92.7 |
| 6 | 0.0 | 30.2 | 0.0 | 89.5 |
| 8 | 0.0 | 21.5 | 0.0 | 86.2 |
| 24 | 0.0 | 8.7 | 0.0 | 56.4 |

Example 26

Comparative Example of Immobilised Est P 1021 and Immobilised Lipase B from *Candida antarctica* (Chirazyme L-2)

TABLE 16

|  | Biocatalyst | |
|---|---|---|
|  | Chirazyme L-2 | Immobilised Est P 1021 |
| Residual activity (%) | 0 | 60 |

Esterase powder (2 mg) prepared as described in Example 13 and Chirazyme L-2 (2 mg, Roche) were heat-treated at 95°

C. for one week under continuous stirring in the presence of an equimolar ratio of methyl laurate and decanol. Afterwards the biocatalyst was recovered and its transesterification reaction rate was determined by GC according to Example 1.3 in the transesterification of methyl laurate with decanol. Chirazyme L-2 lost all its activity under these conditions whereas immobilised Est P 1021 lost only 40% of its initial activity. Results are expressed as relative activities compared to the not heat-treated biocatalysts and are given in Table 16.

Example 27

Production of the Free *Thermococcus* Esterase SEQ ID No:4

In the following the esterase is called Est P 158.

27.1 Culture Medium M21 and Growth Conditions of *Thermococcus* Strain P 158

The medium M21 containing (L-1) was prepared as follows:

| | |
|---|---|
| Yeast Extract | 2 g |
| Casein enzymatic hydrolysate (Sigma P 1192) | 4 g |
| Sea salts | 30 g |
| Cysteine | 0.5 g |
| PIPES | 6.05 g |
| Resazurine(0.1% w/v) | 1 ml |
| Sulphur | 10 g |

The pH was adjusted to 7.5 with NaOH, the medium was heated to 100° C., cooled and dispensed under $N_2/CO_2$ (80/20). Before use the medium was reduced with 2 ml of a sterile anaerobic solution of $Na_2S.9H_2O$ (2% w/v) for 100 ml of M21 medium.

27.2 Production of Est P 158 with the Native *Thermococcus* Strain

For the production of Est P 158 an anaerobic flask containing 2.5 L of medium M21 was prepared. The flask was inoculated with 100 ml of a fresh over-night culture of *Thermococcus* strain P 158 grown under the conditions described in example 27.1. After 16 h of incubation at 80° C., the culture was centrifuged at 8000 g for 15 min at 4° C. The supernatant was discarded and the cells were resuspended in 12.5 mL of flesh M21 medium. The cells were lysed by ultrasonification. 10 cycles with an amplitude at the tip of the horn of 6, 15 cycles with an amplitude of 7 and 3 cycles with an amplitude of 9 were applied. Each cycle was 30 sec with 1 min of pause (Sonicator ultrasonic liquid processor XL, Misonix Incorporated). Cell debris was removed by centrifugation and proteins were recovered in the supernatant Protein concentration was measured according to the Bradford assay, calibrated against bovine serum albumin (M. M. Bradford, Anal. Biochem, 72, (1976) 248). The specific activity was determined according to Example 1.1 to be 8-10 mEU/mg with a stock protein concentration of 4.5-5.5 mg/ml with the following data:
$\Delta E=0.511$; $\epsilon=14200$ $M^{-1}cm^{-1}$; d=0.2 cm; $t_{mon}$=40 min; $f_d$=10

Example 28

Effect of Temperature on Free Est P 158

The activity of the Est P 158 was measured by the assay on hydrolytic activity as described in Example 1.1 except that temperature was varied. Results are shown below as relative activities (Table 17) with an activity at 70° C. taken as 100% for the esterase of the invention.

TABLE 17

| Temperature (° C.) | Residual activity (%) |
|---|---|
| 70 | 100 |
| 80 | 92 |
| 90 | 87 |
| 95 | 75 |

Example 29

Thermostabillty of Free Est P 158

Samples of culture broth prepared as in Example 27.2 were heat-treated at 70° C. in buffered aqueous solution (200 mM PIPES buffer at pH 7.0) for variable incubation times. Est P 158 activity of the heat-treated samples were measured using the hydrolysis assay as described in Example 1.1. Results are expressed as relative activities compared to an unincubated Est P 158 sample and are shown in Table 18.

TABLE 18

| Incubation time at 100° C. (hours) | Residual activity (%) |
|---|---|
| 1 | 98 |
| 2 | 74 |
| 24 | 46 |

Example 30

Solvent Tolerance of Free Est P 158

2 mg free Est P 158 was dissolved in 2 ml of an aqueous solution at pH 7.0 buffered with 100 mM PIPES. The enzyme was incubated at 70° C. under stirring with isopropanol and ethanol at concentrations of 1 M for 40 minutes. Then hydrolytic activity of the enzyme was measured according to Example 1.1 and is given as relative activity referred to a control sample without incubation in organic solvents. Results are shown in Table 19.

TABLE 19

| Organic solvent | Residual activity (%) |
|---|---|
| Isopropanol | 15 |
| Ethanol | 30 |

Example 31

Substrate Specificity of Free Est P 158

The activity of Est P 158 esterase was measured by the assay on hydrolytic activity as described in Example 1.1 except that the temperature is 70° C. and that instead of only C10-HpNPB also the following substrates were tested: (C16-HpNPB), (C18-HpNPB); (C18 oleate-HpNPB). The results are given in Table 20 with activity for C10 taken as 100%.

TABLE 20

| Cn-HpNPB substrate | Relative activity (%) |
|---|---|
| C10 | 100 |
| C16 | 77.3 |
| C18 | 24.1 |
| C18 oleate | 65.7 |

Example 32

Thermostability of Immobilised Native Est P 158

Esterase powder (about 2 mg), prepared as described for Est P 1021 in Example 13, was heat-treated at 70° C. for various incubation times in buffered aqueous solution (200 mM PIPES buffer at pH 7.0). The hydrolytic activity of the heat-treated samples was subsequently measured as described in Example 1.1. Results are given as relative activities compared to an unincubated immobilised Est P 158 sample and are shown in Table 21.

TABLE 21

| Incubation time(day) | Residual activity at 70° C. (%) |
|---|---|
| 1 | 100 |
| 2 | 100 |
| 3 | 100 |

Example 33

Solvent Tolerance of Immobilised Est P 158

| | Residual activity at 70° C. (%) | | |
|---|---|---|---|
| Solvent | 1 day | 2 days | 3 days |
| Water | 70 | 65 | 70 |
| 2-Methyl-2 butanol | 70 | 70 | 85 |
| Methylcyclohexane | 75 | 75 | 70 |

Est P 158 powder (2 mg) prepared as in Example 13 was heat-treated at 70° C. in the presence of various solvents for different times.

Example 34

Cloning of Est P 158

Cloning of Est P 158 was performed as described for Est P 1021 in Examples 3-5.

What is claimed is:

1. An isolated thermostable esterase comprising an amino acid sequence having at least 95% sequence identity to SEQ ID NO:3 or at least 95% sequence identity to SEQ ID NO:4,
wherein said esterase has a catalyzing activity in a temperature range of 70° C. to 95° C., and
wherein said esterase retains at least 80% specific esterase activity as measured by the hydrolysis of a substrate selected from the group consisting of 2-hydroxy-4-p-nitrophenoxy-butyl decanoate and 2-hydroxy-4-p-nitrophenoxy-butyl propionate.

2. An isolated thermostable esterase comprising SEQ ID No: 3, wherein said esterase has a catalyzing activity in a temperature range of 70° C. to 95° C.

3. An isolated thermostable esterase comprising SEQ ID No: 4, wherein said esterase has a catalyzing activity in a temperature range of 70° C. to 95° C.

4. The isolated thermostable esterase according to claim 1 comprising the amino acid motif EAE.

5. The isolated thermostable esterase according claim 4, characterised in that the amino acids directly neighbouring the EAE motif at one or both of the N terminus and C terminus of said motif are selected from the group consisting of E, D, Q, N, H, R, and K.

6. The isolated thermostable esterase according to claim 1, characterised in that the esterase is a recombinant polypeptide.

7. The isolated thermostable esterase according to claim 6, characterised in that the esterase is a free or immobilised polypeptide.

8. The immobilised esterase according to claim 7, wherein the esterase is recycled.

9. The isolated esterase of claim 1, derived from a microorganism of the genera *Pyrococcus* or *Thermococcus*.

10. A method for the production of acyl compounds comprising mixing the esterase of claim 1 with a substrate under conditions sufficient to produce an acyl compound from said substrate, wherein said substrate comprises 2-hydroxy-4-p-nitrophenoxy-butyl-decanoate (C10-HpNPB), 2-hydroxy-4-p-nitrophenoxy-butyl-palmitate (C16-HpNPB), 2-hydroxy-4-p-nitrophenoxy-butyl-stearate (C18-HpNPB), 2-hydroxy-4-p-nitrophenoxy-butyl-oleate (C18'-HpNPB), 2-hydroxy-4-p-nitrophenoxy-butyl-propionate (C3-HpNPB) or 2-hydroxy-4-p-nitrophenoxy-butyl-acetate (C2-HpNPB).

* * * * *

UNITED STATES PATENT AND TRADEMARK OFFICE
CERTIFICATE OF CORRECTION

PATENT NO. : 7,595,181 B2
APPLICATION NO. : 10/954826
DATED : September 29, 2009
INVENTOR(S) : Grüning et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 824 days.

Signed and Sealed this

Twenty-eighth Day of September, 2010

David J. Kappos
*Director of the United States Patent and Trademark Office*